(12) United States Patent
Wilson et al.

(10) Patent No.: US 9,134,243 B2
(45) Date of Patent: Sep. 15, 2015

(54) SYSTEM AND METHOD FOR SUB-SURFACE FLUORESCENCE IMAGING

(75) Inventors: Brian Campbell Wilson, Toronto (CA); Anthony Taywon Kim, Toronto (CA)

(73) Assignee: UNIVERSITY HEALTH NETWORK, Toronto (CA)

( * ) Notice: Subject to any disclaimer, the term of this patent is extended or adjusted under 35 U.S.C. 154(b) by 150 days.

(21) Appl. No.: 13/516,977

(22) PCT Filed: Dec. 17, 2010

(86) PCT No.: PCT/CA2010/002082
§ 371 (c)(1),
(2), (4) Date: Sep. 7, 2012

(87) PCT Pub. No.: WO2011/072401
PCT Pub. Date: Jun. 23, 2011

(65) Prior Publication Data
US 2012/0326055 A1  Dec. 27, 2012

Related U.S. Application Data

(60) Provisional application No. 61/287,997, filed on Dec. 18, 2009.

(51) Int. Cl.
*G01J 1/58* (2006.01)
*G01N 21/64* (2006.01)
(Continued)

(52) U.S. Cl.
CPC .......... *G01N 21/6458* (2013.01); *A61B 5/0059* (2013.01); *A61B 5/0071* (2013.01); *A61B 5/415* (2013.01); *A61B 5/418* (2013.01);
(Continued)

(58) Field of Classification Search
CPC .................................................. G01N 21/6428
USPC ........................................................ 250/459.1
See application file for complete search history.

(56) References Cited

U.S. PATENT DOCUMENTS 6,175,759 B1  1/2001  Chan et al.
2005/0143662 A1*  6/2005  Marchitto et al. ............ 600/473
(Continued)

OTHER PUBLICATIONS

Kim et al., "Quantitative and Depth-Resolved Fluorescence Techniques for Introperative Guidance of Brain Tumor Resection Surgery," J. Biomed. Optics, pp. 1-3, 2010.
(Continued)

*Primary Examiner* — David Porta
*Assistant Examiner* — Hugh H Maupin
(74) *Attorney, Agent, or Firm* — Nixon Peabody LLP; David S. Resnick; Leena H. Karttunen Contarino

(57) ABSTRACT

A system for sub-surface fluorescence imaging is provided, the system comprising: an excitation source for selectably emitting light at at least one of at least two excitation wavelengths or wavelength ranges at a target surface; and a light detector for detecting fluorescence emission wavelengths or wavelength ranges from the target surface; wherein at least one of the at least two excitation wavelengths or wavelength ranges causes fluorescing of at least one marker at a sub-surface depth, the emitted light at each of the at least two excitation wavelengths or wavelength ranges having different depths of optical penetration and causing fluorescing at respective different depths. A method for sub-surface fluorescence imaging is also provided, in some cases exemplified by a reconstruction of the sub-surface fluorescence topography.

22 Claims, 40 Drawing Sheets

(51) Int. Cl.
- A61B 5/00 (2006.01)
- G01J 3/02 (2006.01)
- G01J 3/10 (2006.01)
- G01J 3/44 (2006.01)
- G02B 21/16 (2006.01)
- G02B 21/36 (2006.01)
- G07D 7/12 (2006.01)

(52) U.S. Cl.
CPC *A61B 5/445* (2013.01); *G01J 3/02* (2013.01); *G01J 3/0218* (2013.01); *G01J 3/10* (2013.01); *G01J 3/4406* (2013.01); *G02B 21/16* (2013.01); *G02B 21/367* (2013.01); *G07D 7/122* (2013.01); *G07D 7/128* (2013.01); *A61B 2562/0242* (2013.01); *G01N 2021/6419* (2013.01)

(56) References Cited

U.S. PATENT DOCUMENTS

2007/0016078 A1* 1/2007 Hoyt et al. .................. 600/476
2007/0158585 A1* 7/2007 Hall et al. .................. 250/458.1

OTHER PUBLICATIONS

Kim et al., "Topographic mapping of subsurface fluorescent structures in tissue using multiwavelength excitation," J. Biomed. Optics, vol. 15, Issue 6, pp. 066026-1-066026-7, 2010.

* cited by examiner

SYSTEM AND METHOD FOR SUB-SURFACE FLUORESCENCE IMAGING

CROSS REFERENCE TO RELATED APPLICATION

This application is a 35 U.S.C. §371 National Phase Entry Application of International Application No. PCT/CA2010/002082, filed Dec. 17, 2010, which designates the United States, and which claims benefit under 35 U.S.C. §119(e) of the U.S. provisional application No. 61/287,997, filed on Dec. 18, 2009, the contents of which are herein incorporated by reference in their entirety.

TECHNICAL FIELD

The present disclosure relates to the technical field of fluorescence imaging. In particular, the present disclosure relates to the technical field of sub-surface fluorescence imaging.

BACKGROUND

Various methods have been proposed to solve the general depth-resolved fluorescence problem in optically-turbid media such as tissue. Point-detection methods have been developed, such as using the depth-dependent distortion of the fluorescence emission spectrum by tissue absorption (Swartling et al., 2005) or using spatially-resolved diffuse fluorescence to determine depth (Hyde et al., 2001).

Since there may be limitations to point detection methods in a surgical field, wide-field methods have also been pursued. One method has the diffuse fluorescence pattern imaged using broad-beam illumination, with the rather restrictive modeling assumption that the fluorescence source is point-like (Comsa et al., 2008). Laminar optical tomography has also been developed for full three-dimensional reconstruction, where a laser is raster-scanned over the tissue surface and the diffuse fluorescence pattern imaged at each xy point (Hillman et al., 2004; Kepshire et al., 2007). The major issue with optical tomography (i.e. full 3-D reconstructions) is that it is generally accepted to be an ill-posed problem (Arridge, 1999); as well, the data may be corrupted by uneven tissue surfaces or tissue movement during the long acquisition times.

SUMMARY

In some aspects, the present disclosure describes a system and method for sub-surface fluorescence imaging. In some examples, fluorescence detection and mapping in optically-turbid media is described, including the use of fluorescence to localize the depth of sub-surface fluorescence within media such as biological tissue. The surface of a sub-surface object (e.g., a top surface or top surface layer, closest to an exposed target surface of the media) may be imaged to produce a depth-resolved topographical image. Fluorescence may be endogenous to a target (e.g., tissue) or due to an exogenously applied fluorescent agent. In some examples, the disclosed system and method may be useful for guidance during tumor resection surgery, as well as to locate buried blood vessels, lymph nodes or other structures, as well as other biological and non-biological applications.

In some aspects, the present disclosure provides a system for sub-surface fluorescence imaging. In particular, the system may be used to extract depth-resolved topographical information of sub-surface fluorescence in optically turbid media, for example where the medium is biological tissue. In general, different wavelengths of light penetrate at different depths in turbid media if there is a wavelength dependence of optical attenuation. This behavior may be used to extract the sub-surface fluorescence topography (SSFT) of buried fluorescing objects. By capturing fluorescence images at different excitation wavelengths for illumination, a topographical map of the buried fluorescence, with depth resolution, may be reconstructed, for example using an algorithm based on the physics of light transport in optically turbid (i.e. light absorbing and scattering) medium. Thus, the depth of a fluorescing object, such as a fluorescing tumor, below a target surface can be determined. In some cases, the average optical absorption and elastic scattering properties of the target media (e.g., tissue), may determine a maximum depth for this imaging. The disclosed system may be used with, for example, fluorescence image-guided surgery based on the detection of residual tumor lying beneath the target surface (e.g., the open surgical field).

In some aspects, there is provided a system for sub-surface fluorescence imaging comprising: an excitation source for selectably emitting light at at least one of at least two excitation wavelengths or wavelength ranges at a target surface; and a light detector for detecting fluorescence emission wavelengths or wavelength ranges from the target surface; wherein each of the at least two excitation wavelengths or wavelength ranges causes fluorescing of at least one marker at a sub-surface depth, the emitted light at each of the at least two excitation wavelengths or wavelength ranges having different depths of optical penetration and causing fluorescing at respective different depths.

In some aspects, there is provided a method for sub-surface fluorescence imaging comprising: illuminating a target surface with light at at least two excitation wavelengths or wavelength ranges; wherein at least one of the at least two excitation wavelengths or wavelength ranges causes fluorescing of at least one marker at a sub-surface depth, the light at each of the at least two excitation wavelengths or wavelength ranges having different depths of optical penetration and causing fluorescing at respective different depths; detecting fluorescence emission wavelengths or wavelength ranges from the target surface; determining a fluorescence calculation for each of the at least two excitation wavelengths or wavelength ranges using the detected fluorescence emission wavelengths or wavelength ranges; and constructing a sub-surface fluorescence topographical image using the determined fluorescence calculations.

BRIEF DESCRIPTION OF THE DRAWINGS

Reference will now be made to the drawings, which show by way of example embodiments of the present disclosure, and in which.

DETAILED DESCRIPTION

In some aspects, the present disclosure may be useful for recovering topographic maps (i.e., maps having depth-resolution) of sub-surface fluorescing objects. The disclosed technique may be based on imaging the surface with wide-field excitation at several wavelengths or wavelength ranges. A light transport model (such as diffusion theory, Monte Carlo, empirical techniques, or any other suitable model) may be used to extract the depth of the upper surface of buried fluorescing objects from this set of multispectral excitation images. The model may be based on the wavelength dependence of the optical depth penetration of the overlying media (e.g. biological tissue) due to the wavelength dependence of the optical absorption and elastic scattering.

In some examples, the disclosed imaging system is used to produce fluorescence images at different excitation wavelengths or wavelength ranges and example algorithms to process raw data to reconstruct sub-surface fluorescence topographical maps of buried fluorescing objects are described.

In some examples, the system for sub-surface fluorescence imaging includes an excitation source and a light detector. The excitation source selectably emits light at at least one of at least two excitation wavelengths or wavelength ranges at a target surface. In some examples, there are more than two excitation wavelengths or wavelength ranges, and in some examples the excitation source may emit a plurality of such wavelengths or wavelength ranges simultaneously. The light detector detects fluorescence wavelengths or wavelength ranges from the target surface. At least one of the at least two wavelengths causes fluorescing of at least one marker at a sub-surface depth. Each of the at least two excitation wavelengths or wavelength ranges has a different depth of penetration and causes fluorescing at a respective different depth. In some examples, the marker may be a biomarker or a non-biological marker. A biomarker in this example may include a particular tissue type, or a fluorescent agent that targets certain tissue types. Although the present disclosure refers to a biomarker in the examples, it should be understood that the description may apply equally to a non-biological marker. In general, the system typically employs wide-field, multi-spectral excitation imaging to detect depth-dependent information for constructing a sub-surface fluorescence topographical image. In the present disclosure, a topographical image may refer to an image having depth resolution—that is, an image providing information about the depth of the imaged features.

Figure 1:
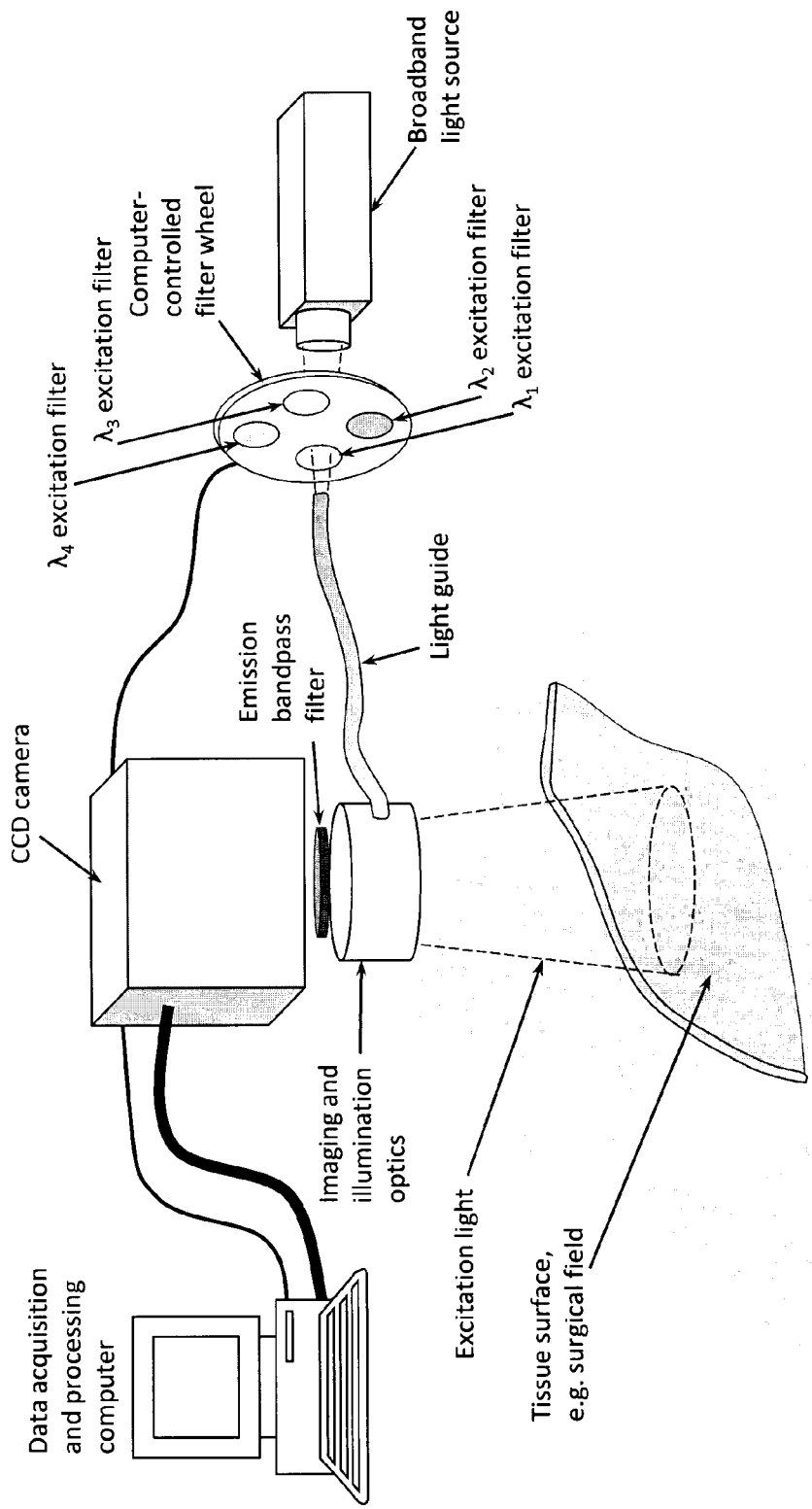
FIG. 1 is a schematic of an example imaging system that may be used to produce multispectral excitation images.

FIG. 1 shows an example system (in this example, the light detector is a charge-coupled device camera) that may be suitable for visualizing fluorescence emissions from a target surface. In the example shown, the excitation source includes a broadband light source (e.g. xenon or mercury arc lamp, LED bank, filament lamp, or any other suitable source) filtered by excitation bandwidth filters mounted in a computer-controlled filter wheel. The filters here are labeled $\lambda_1$, $\lambda_2$, $\lambda_3$ and $\lambda_4$, although in other examples more or fewer than four filters may be used to obtain correspondingly more or fewer excitation bands. The excitation source includes a light guide. The filtered excitation light is channeled through the light guide (e.g. liquid light guide, fiberoptic cable or other suitable light guide) to be sent through illumination optics that are designed such that the excitation light is directed to the target surface (e.g. tissue such as skin, surgical field or wound). In other examples, a light guide is not used and the excitation light is transmitted through free-space. In another example, light from the broadband light source may be channeled to the illumination optics via the light guide first, and the excitation filter wheel mounted to the illumination optics for filtering the channeled broadband light. In another example, another method of selecting excitation wavelengths or wavelength ranges may be used, such as an acousto-optic tunable filter, liquid crystal tunable filter, diffraction grating in combination with an angular actuator and slit, a linear actuator that places filters in line with the broadband light source, or any other suitable filtering method. In some examples, the excitation filter may also be a continuously spectrally-varying filter which may be used to select wavelengths based on spatial position relative to the broadband light source beam. In the example of FIG. 1, the re-emitted light from the target surface is collected by a light detector, in this case imaging optics that focuses the light on a CCD camera or similar imaging device. In some cases, the light detector may include a detection filter restricting the wavelengths detected. In this example, prior to striking the CCD camera, the light is passed through an emission bandpass filter to reject the excitation band and let in only the fluorescence light. The CCD and the filter wheel may be controlled, for example by a computer or a processor, to take an image per excitation wavelength, sequentially.

In some examples, instead of a broadband light source with selectable filters, the excitation source may include a monochromator. An example of a monochromator is a diffraction grating in combination with a variable (e.g., mechanically selectable) slit that can vary the excitation wavelengths or wavelength ranges (e.g., both the actual wavelength and the width of the wavelength range) emitted.

In the example shown, the light entering the imaging device is filtered via a bandpass emission filter, for example, in the range of about 500 nm to about 900 nm, in the range of about 600 nm to about 850 nm, in the range of about 650 nm to about 750 nm, or about 700 nm, in order to reject the excitation light such that only fluorescence is collected. Typically, in this example, the excitation light is directed at the camera's field of view as parallel as possible to the camera's optical axis but with some angular tolerance within a few degrees, say 15°, from the optical axis. The excitation light is one of multiple wavelength ranges that sequentially impinge upon the target surface, for example, excitation bands with central wavelengths of around 405, 495, 546 and 625 nm (violet, cyan, green and red, respectively). The excitation wavelengths or wavelengths bands may be any wavelength, including infrared, visible and ultraviolet wavelengths, for example including wavelengths in the range of about 380 nm to about 900 nm, about 390 nm to about 420 nm, about 480 nm to about 510 nm, about 530 nm to about 560 nm, about 610 nm to about 640 nm, about 680 to about 720, about 720 to about 770, and combinations thereof. Throughout this disclosure, "excitation wavelength" and "excitation wavelength range" may be used interchangeably to describe either an illumination with a single wavelength or with a central wavelength and a bandwidth. Although specific wavelengths are described, it should be understood that this may also refer to a wavelength range near or around the specific wavelengths. In general, it should be understood that references to a wavelength may equally be applied to a wavelength range and vice versa.

In FIG. 1, the excitation wavelength ranges are selectable via a computer-controlled filter wheel coupled to a broadband light source, with excitation filters mounted in the filter wheel to provide the desired spectral ranges. Here, the excitation wavelength ranges are specified as $\lambda_1$, $\lambda_2$, $\lambda_3$ and $\lambda_4$. A computer selects an excitation wavelength and then signals the detector to acquire an image. This is done sequentially for each wavelength range. Since fluorescence signals may be weak, acquisition time may be seconds for each image. The resulting data are fluorescence images corresponding to each of the excitation wavelength ranges, with fluorescence imaged at the single emission wavelength band.

Figure 2:
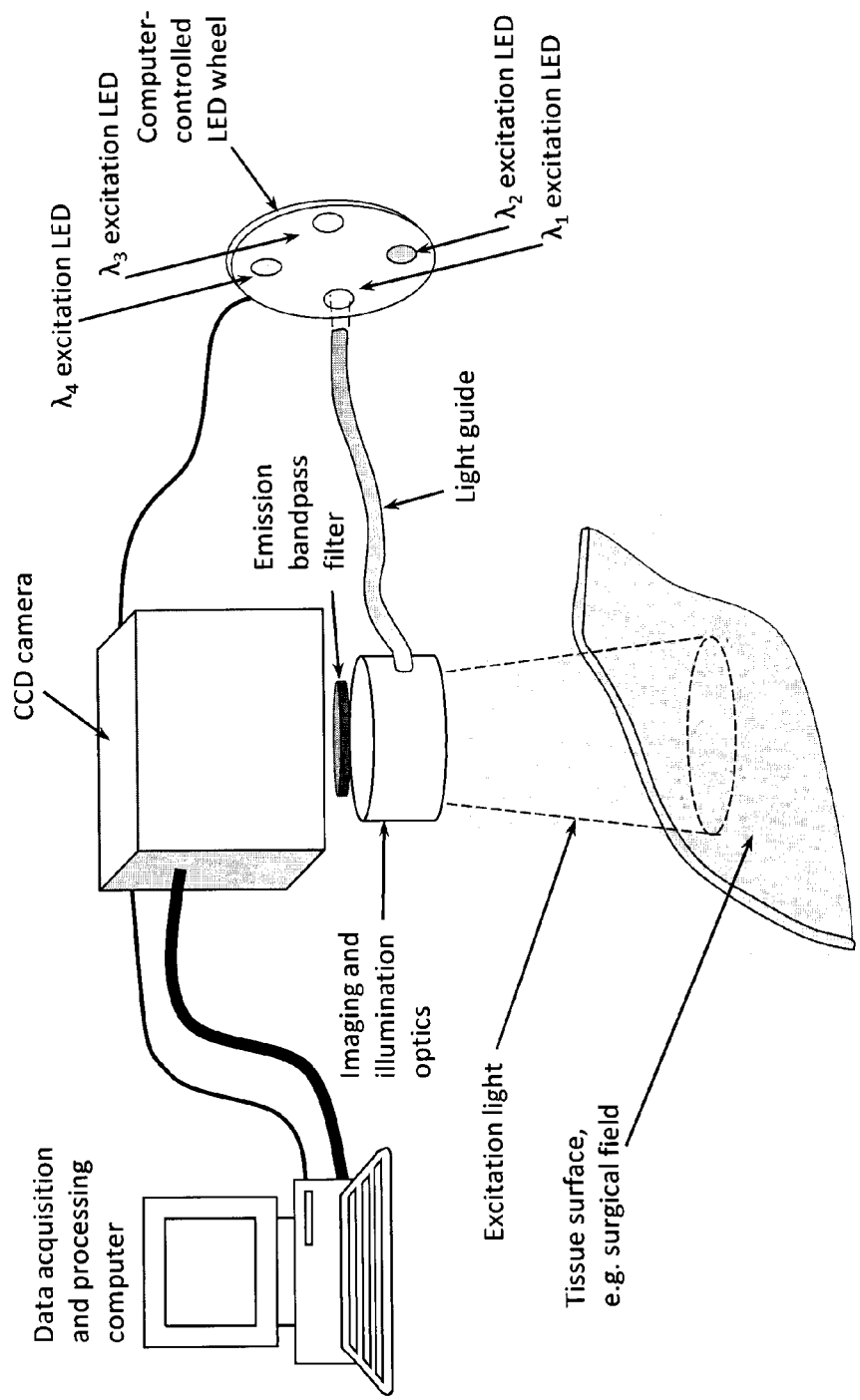
FIG. 2 is a schematic of another example imaging system that may be used to produce multispectral excitation images.

In another example, the wavelength range of the excitation light may be selectable in a manner as shown in the example system of FIG. 2. Here, the broadband light source and the filter wheel is replaced by a wheel (e.g., computer-controlled or otherwise automated) with LEDs mounted to it in such a manner that at a selected wheel position the light from an LED can be coupled to the light guide leading to the illumination optics. In this example, LEDs are used rather than the filtered broadband excitation light source of FIG. 1. A computer-controlled positioning device, such as a wheel, can be used to position each LED in a manner that can couple the LED to the light guide. Each LED may cover a wavelength range, but may have narrow peaks. Peak wavelengths for LEDs may include, for example, 405, 505, 546 and 635 nm. The LED wheel may be replaced by any mechanical actuator that can switch the LED that is coupled to the light guide. Alternatively, the light guide may be a splitter cable, with each split end coupled to an LED of different wavelength, with the excitation wavelengths controlled by switching one LED on with the others turned off. Monochromatic lasers or other relatively narrow wavelength sources may be used in place of LEDs.

Figure 3:
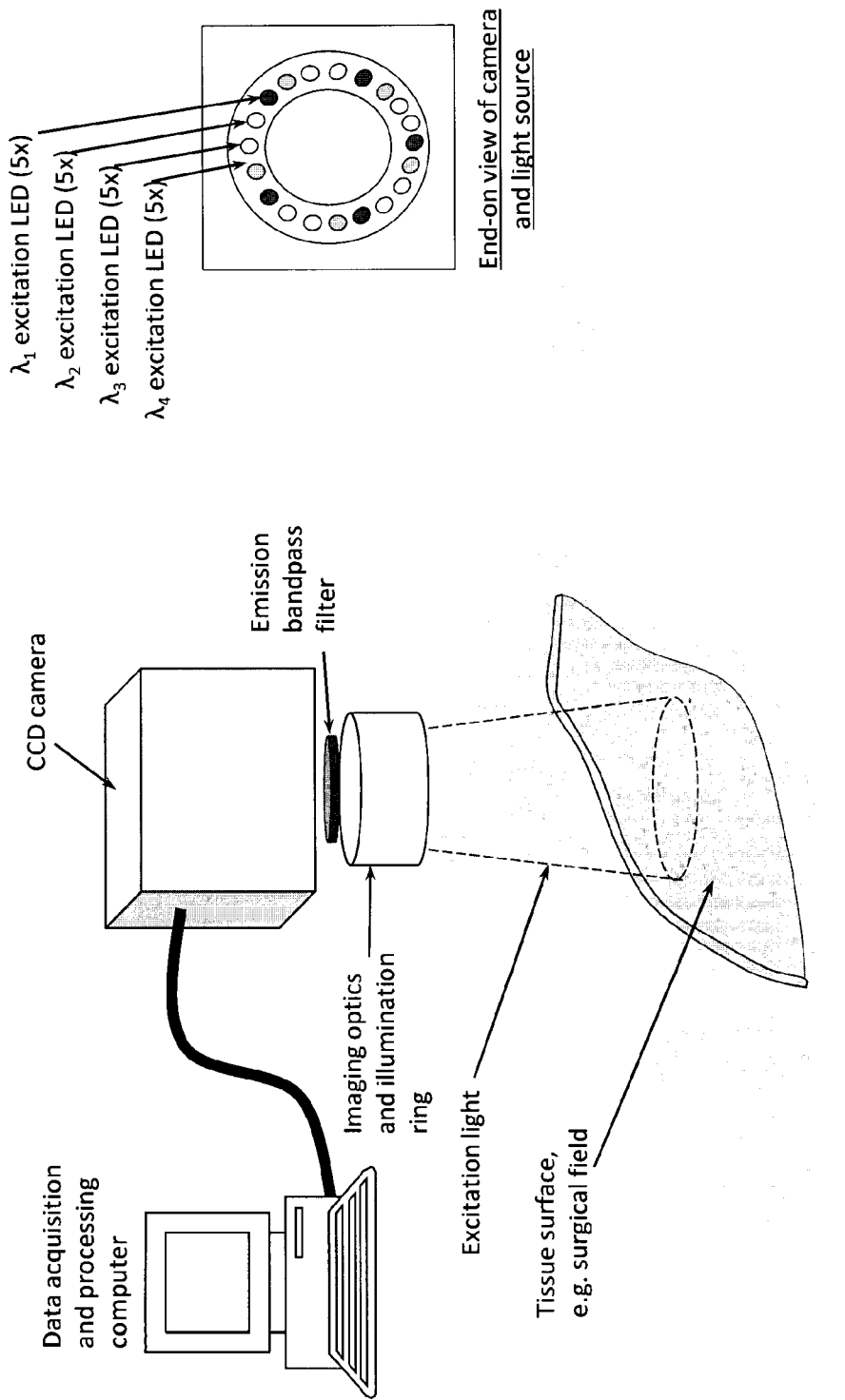
FIG. 3 is a schematic of another example imaging system that may be used to produce multispectral excitation images.

Another example system is shown in FIG. 3, which is similar to the system of FIG. 1 except the illumination source is a ring of light-emitting diodes (LEDs) coaxial to the imaging optics. Here, there are five LEDs of each excitation wavelength staggered at intervals around the LED ring as shown in the end-on view of the camera and light source, although five are shown, there may be more or fewer LEDs per wavelength, or more or fewer LED wavelengths. The LEDs are controlled (e.g., via computer) to turn on one wavelength at a time as the CCD camera acquires each excitation image. In this example, a ring of LEDs surrounds the imaging optics in a manner such that the LEDs illuminate the target surface. LEDs of different wavelength ranges are staggered at intervals in such a way that the tissue is illuminated relatively uniformly. The excitation wavelength illuminating the target surface may be controlled electronically, with all of the LEDs of a kind turned on sequentially. In other examples, the wavelength may be controlled by other means, including manually, optically or mechanically.

In some examples (e.g., the examples shown in FIG. 1, FIG. 2 and FIG. 3), multiplexed spectral scanning may also be used, for example, to modulate each wavelength at a different frequency to frequency-encode the excitation wavelength so that all wavelengths can be used simultaneously. This may be useful in applications where the target is not static, but moving or changing in some fashion.

It may be useful to limit background light collected by the imaging device. A source of background is from bleed-through light in between the excitation and emission channels. One possibility to compensate for excessive background is to measure a reflectance image in addition to the multispectral fluorescence images. This can be achieved by illuminating the target surface with light over a major portion of the detected emission wavelengths or wavelength ranges (e.g., white light). For example, in the embodiment shown by FIG. 1, one of the positions in the filter wheel may have either free space or a neutral density filter mounted to it. The white light reflectance image can be used in conjunction with a known signal-to-background ratio to subtract the background from acquired fluorescence images. In some examples, this background subtraction can be performed using any suitable method, for example directly to the raw image data, or during or after post-processing computation, such as that described below.

EXAMPLES

Figure 4:
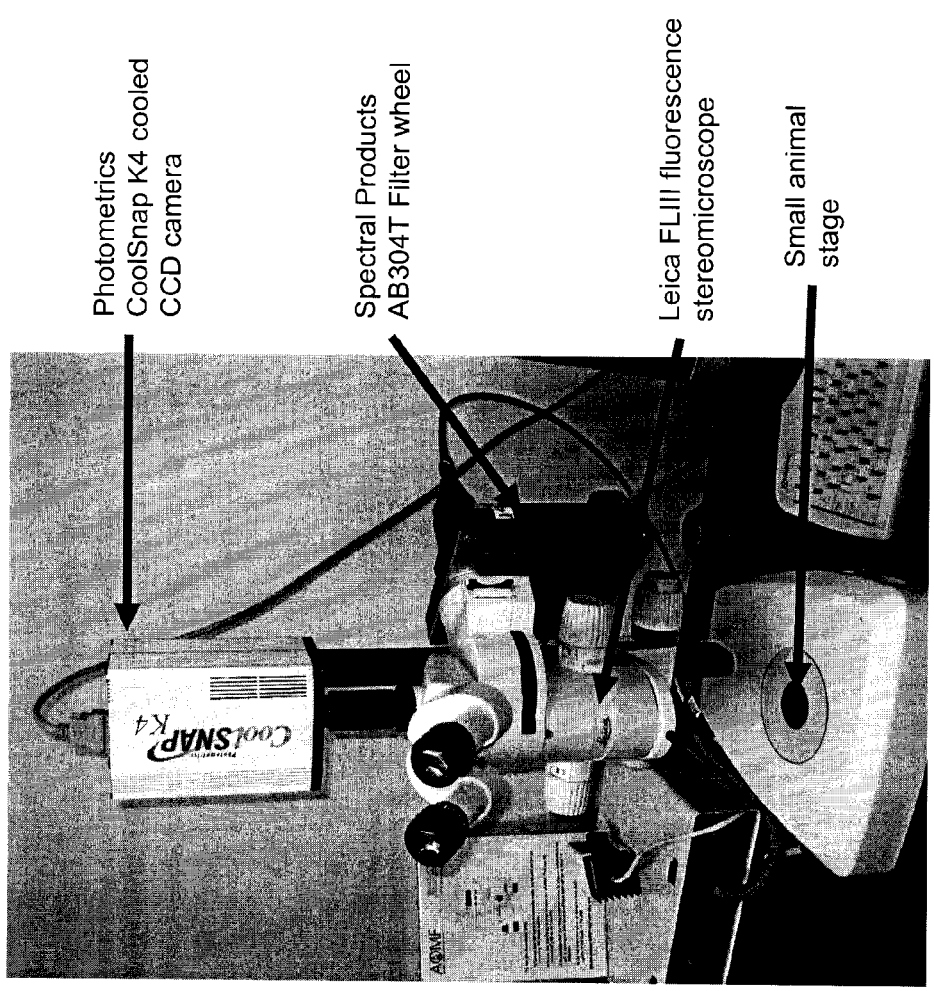
FIG. 4 is a photograph of an example small-animal imaging system built according to the schematic of FIG. 1.

FIG. 4 shows an example system suitable for small animal imaging, similar to the example shown in FIG. 1. In this example, the imaging and illumination optics were from a fluorescence epi-illumination stereomicroscope. The excitation light was provided by a mercury arc lamp (not shown) coupled via liquid light guide to a computer-controlled filter wheel, which was connected to the excitation port of the stereomicroscope. A cooled CCD was used to acquire the images. A PC computer was used to sequentially move the filter wheel position and acquire images with the CCD at each excitation wavelength.

In some examples, the system may be configured to be suitable for human surgical applications. In one example, the system included an epifluorescence microscope (MZ FLIII: Leica, ON, Canada) custom retrofitted with a 12-channel filter wheel (AB304T: Spectral Products, CT, USA) that filters a mercury arc lamp white-light source (X-Cite 120: Exfo, TX, USA) for the fluorescence excitation. Fluorescence filters may be selected to image protoporphyrin IX (PpIX), which can be enhanced with the systemic administration of 5-aminolevulinic acid (ALA). In some examples, PpIX may be induced in highly metabolic cells by systemic administration of ALA, that is, the PpIX may be ALA-induced PpIX. PpIX is involved in the heme biosynthesis pathway, and has been shown to be a useful marker for highly metabolic, malignant tumor cells. Excitation bandpass filters (Chroma, VT, USA) may be used with central wavelengths of 405, 495, 546 and 625 nm and bandwidths (full width at half maximum, FWHM) of 20, 32, 28 and 47 nm, respectively. These wavelengths correspond approximately to PpIX excitation peaks, as seen in FIG. 5.

Figure 5:
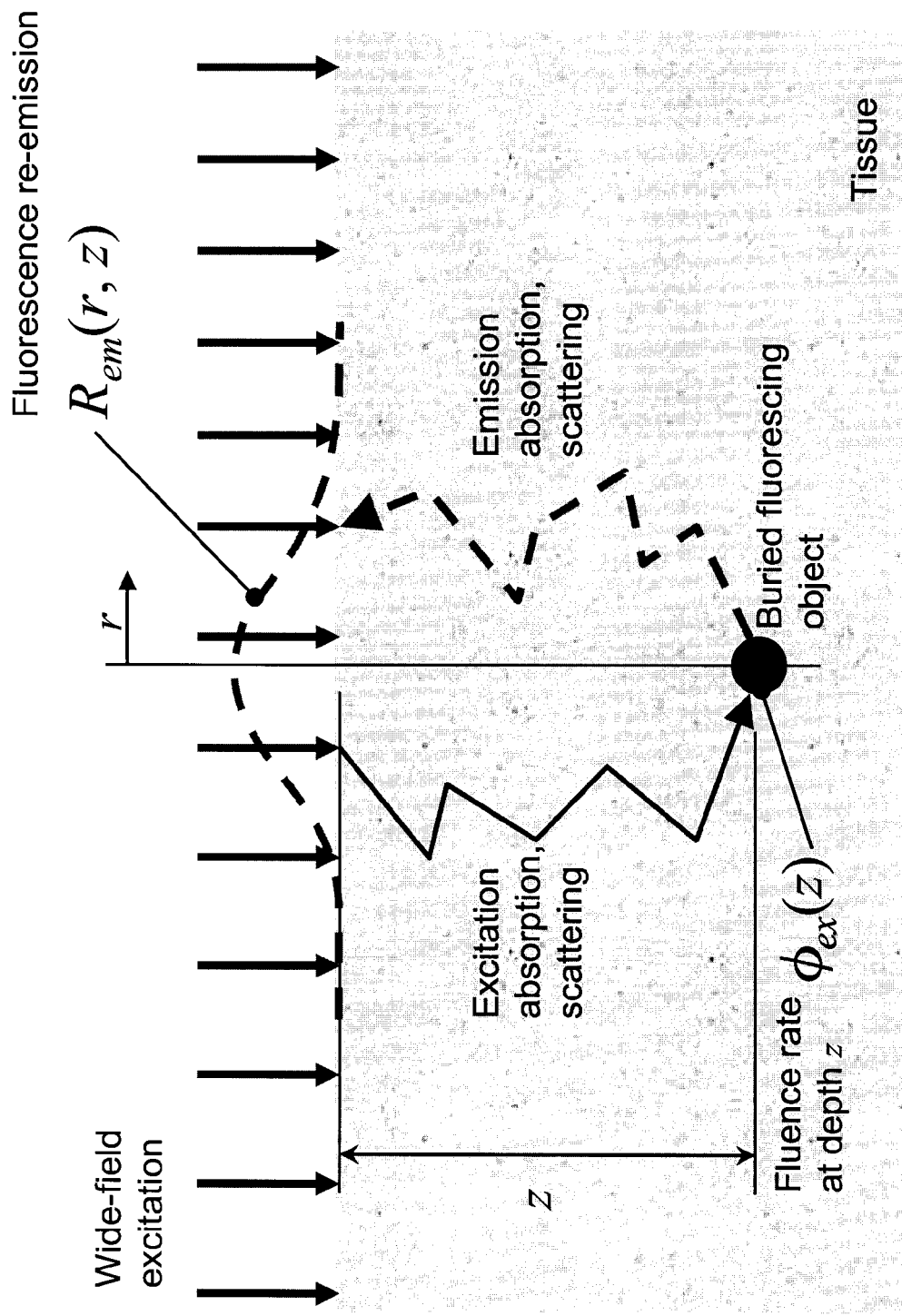
FIG. 5 is a schematic of an example of photon transport through tissue.

FIG. 5 illustrates an example of photon transport through tissue. In the example shown, wide-field excitation light impinges on the target surface, with a portion of the light entering the tissue. The light in tissue undergoes transport scattering and absorption at the excitation wavelength. The fluence rate, $\phi(z)$, is dependent on depth, z. A buried fluorescing object at depth z fluoresces, that is, it absorbs some of the excitation light at depth z and re-emits at a longer wavelength. The fluorescence re-emission at the surface is collected by the imaging optics. This light transport model may be suitable for an algorithm to determine fluorescence depth in tissue.

Referring back to FIG. 4, in this example, the excitation power was in the range 3-11 mW, over a 1 cm Gaussian spot (FWHM) at the target surface. The target surface (in this example, a tissue surface) was in the range of 2-10 cm from the microscope lens. A cooled CCD camera (CoolSnap K4: Photometrics, AZ, USA) mounted on the microscope served to image the fluorescence emission. A corresponding white-light image was also taken for anatomical reference. A 700 nm bandpass filter (50 nm FWHM) was used in front of the camera to block the excitation light and pass the PpIX fluorescence. The mechanical selection of excitation filters and acquisition of the corresponding images in this example was automated (e.g., by a software module).

Method

An example method for sub-surface fluorescence imaging is now described. This method may be based on raw image data acquired using the system described above. The example method includes: illuminating a target surface with light at at least two excitation wavelengths or wavelength ranges; detecting fluorescence emission wavelengths or wavelength ranges from the target surface; determining a fluorescence calculation for each of the at least two excitation wavelengths or wavelength ranges using the detected fluorescence emission wavelengths or wavelength ranges; and constructing a sub-surface fluorescence topographical image using the determined fluorescence calculations. At least one of the at least two excitation wavelengths or wavelength ranges causes fluorescing of at least one biomarker at a sub-surface depth, and light from each of the at least two excitation wavelengths or wavelength ranges has different depths of optical penetration and cases fluorescing at respective different depths. In some examples of the method, at least two of the excitation wavelengths or wavelength ranges cause fluorescing of the biomarker (e.g., in the ratiometric technique described below), while in other examples, the method may be carried out where at least one of the excitation wavelengths or wavelength ranges causes fluorescing of the biomarker (e.g., in the discrete range technique described below). Although the disclosed method and system is described for constructing a sub-surface fluorescence topographical image, it should be understood that the disclosed method and system may also be suitable for sub-surface fluorescence topographical point-measurements. That is, the image may be a single pixel, to provide for single-point detection (e.g., using a fiberoptic probe). In general, all discussion referencing a sub-surface fluorescence topographical image may also apply to a sub-surface fluorescence topographical point-measurement.

Construction of the sub-surface fluorescence topographical image may be based on a model of sub-surface fluorescence. The sub-surface fluorescence topographical image is a depth-resolved image, including depth information for the imaged features. The specific model used affects the fluorescence calculation that should be made for each excitation wavelength. Example models and their use are described below.

Model

Example models and algorithms suitable for producing sub-surface fluorescence topographic maps using multispectral excitation image data (e.g., that acquired by the system described above) are now described, including what may be referred to as a ratiometric technique. Although certain models, equations and theories are described, these are for the purpose of illustration only and the present disclosure is not bound to any such models, equations or theories. Variations may be made within the scope of the present disclosure. For the following discussion, the subscripted notations x and m refer to the excitation and emission wavelengths (or wavelength ranges), respectively.

The fluorescence surface emission, $F_m$, from fluorophore at depth z below the target surface is given by $$F_m(r,z) = E_x \eta_m \mu_{af,x} Q_{x,m} S_f \phi_x(z) R_m(r,z), \quad (1)$$

where $E_x$ is the excitation irradiance, $\eta_m$ is a constant that incorporates the optical efficiency of the collection chain (camera+optics+emission filter transmission), $S_f$ is a source factor that is dependent on the shape and other miscellaneous properties of the fluorescing object, $\phi_x(z)$ is the normalized fluence rate, and $R_m$ is the normalized re-emission profile. The independent variable r denotes that both $F_m$ and $R_m$ are spatially distributed in the xy (target surface) plane. The fluorophore has an excitation absorption coefficient, $\mu_{af,x}$, and a wavelength-dependent fluorescence quantum yield, $Q_{x,m}$.

Using the signal at one of the excitation wavelengths as a reference, many of the terms in Eq. (1) cancel out (namely, $\eta_m$, $S_f$ and $R_m$), leaving a depth-dependent metric, which is essentially the ratio between the excitation fluence rates at different wavelengths. In an example, the fluorescence due to the 405, 546 and 495 nm excitations (in order of decreasing effective attenuation coefficient of the tissue at the excitation wavelength, $\mu_{eff,x}$) were used as the signal, and the fluorescence due to the 625 nm excitation (corresponding to the lowest $\mu_{eff}$) was used as the reference. This generated three fluorescence ratio metrics, $M_1 = \alpha_1 F_{405nm}/F_{625nm}$, $M_2 = \alpha_2 F_{546nm}/F_{625nm}$ and $M_3 = \alpha_3 F_{495nm}/F_{625nm}$, where $$\alpha_1 = (E_{625nm} \mu_{af,625nm} Q_{625nm,700nm}) / (E_{405nm} \mu_{af,405nm} Q_{405nm,700nm})$$

$$\alpha_2 = (E_{625nm} \mu_{af,625nm} Q_{625nm,700nm}) / (E_{546nm} \mu_{af,546nm} Q_{546nm,700nm})$$

$$\alpha_3 = (E_{625nm} \mu_{af,625nm} Q_{625nm,700nm}) / (E_{495nm} \mu_{af,495nm} Q_{495nm,700nm}) \quad (2)$$

The normalization coefficients $\alpha_1$, $\alpha_2$ and $\alpha_3$ may be obtained by imaging the target fluorophore in free space (i.e. not buried in turbid media, or at z=0) at the multiple excitation wavelengths, such that $\alpha_1 = (F_{625nm}/F_{405nm})|_{z=0}$, etc. Note that the ratios $M_1$, $M_2$ and $M_3$ may have several different forms, and does not always require having the same reference excitation wavelength in the denominator. For example, an alternative ratio format would be $M_1'=\alpha_1'F_{405nm}/F_{546nm}$, $M_2'=\alpha_2'F_{546nm}/F_{495nm}$ and $M_3'=\alpha_3'F_{495nm}/F_{625nm}$ [the prime (') notation simply denotes that these formulations are different than the previous ratiometric definitions]. Techniques using these ratio metrics may be referred to as ratiometric techniques.

Analytic expressions for $\phi_x(z)$ based on diffusion theory can be used as the light-transport model (Farrell et al., 2003). A general solution to the diffusion theory differential equation is $$\phi_x(z) = A\exp(-\mu_{eff,x}z) + B\exp(-\mu'_{t,x}z), \quad (3)$$

where $\mu_{eff,x} = \sqrt{3\mu_{a,x}\mu'_{t,x}}$ is the effective attenuation coefficient and $\mu'_{t,x} = \mu_a + \mu_s'$ is the transport coefficient, with everything in terms of the excitation wavelength. The terms A and B result from solving the diffusion theory equation using boundary conditions at the target surface that is created due to the index mismatch between air and the tissue. The coefficient K quantifies this index mismatch:

$$K = \left(\frac{1+R_j}{1-R_\phi}\right), \quad (4)$$

and $$R_\phi = \frac{1}{\pi}\int_{2\pi} R_{Fresnel}(\theta)\cos(\theta)d\Omega \quad (5)$$

$$R_j = \frac{3}{\pi}\int_{2\pi} R_{Fresnel}(\theta)\cos^2(\theta)d\Omega,$$

with $R_{Fresnel}$ the unpolarized Fresnel reflection coefficient. For example, a value suitable for biomedical optics is $n_{tissue}=1.4$, resulting in $R_\phi=0.529$ and $R_j=0.389$.

$$A = \frac{-\mu'_{s,x}(1+2KD_x\mu'_{t,x})}{(1+2KD_x\mu_{eff,x})(\mu_{a,x} - D_x\mu'^2_{t,x}) - (1+2KD_x\mu'_{t,x})(\mu_{a,x} - D_x\mu^2_{eff,x})} \quad (6)$$

$$B = \frac{\mu'_{s,x}(1+2KD_x\mu_{eff,x})}{(1+2KD_x\mu_{eff,x})(\mu_{a,x} - D_x\mu'^2_{t,x}) - (1+2KD_x\mu'_{t,x})(\mu_{a,x} - D_x\mu^2_{eff,x})} \quad (7)$$

These diffusion theory-derived equations may be used for calculation of the fluence rate at depth, although there are other methods that may be used for this calculation, such as Monte Carlo, empirical methods, or other suitable methods. In some cases, Monte Carlo simulations may be used because Monte Carlo may provide more accurate results closer to the target surface than the diffusion theory solution.

Note that in principle, only two wavelengths are required for a depth calculation, however more than two wavelengths may be used. The use of more than two wavelengths may be useful for better xy spatial resolution near the surface for excitation wavelengths with high tissue absorption. It may be useful to span a relatively wide range of both spatial resolution and depth penetration. In an example, the algorithm applied to retrieve the depth estimate of the fluorophore (tumor) surface was as follows:

1. Use the depth estimate from $M_1$ if $M_1>T$, else go to 2.
2. Use the depth estimate from $M_2$ if $M_2>T$, else go to 3.
3. Use the depth estimate from $M_3$.

where T is a threshold value where the ratiometric signal is too low to provide a reliable depth estimation. In some examples, the threshold value of 0.05 was selected as the cut-off point. Note that prior to calculation, the reference wavelength (i.e. the wavelength range in the denominator) in this case the excitation at a central wavelength of 625 nm, may have all pixels near the background signal changed to a relatively large number, say ten times the saturation value, to help avoid the condition where there are very small or zero numbers in the denominator. The technique described above is referred to as the ratiometric method.

Figure 6:
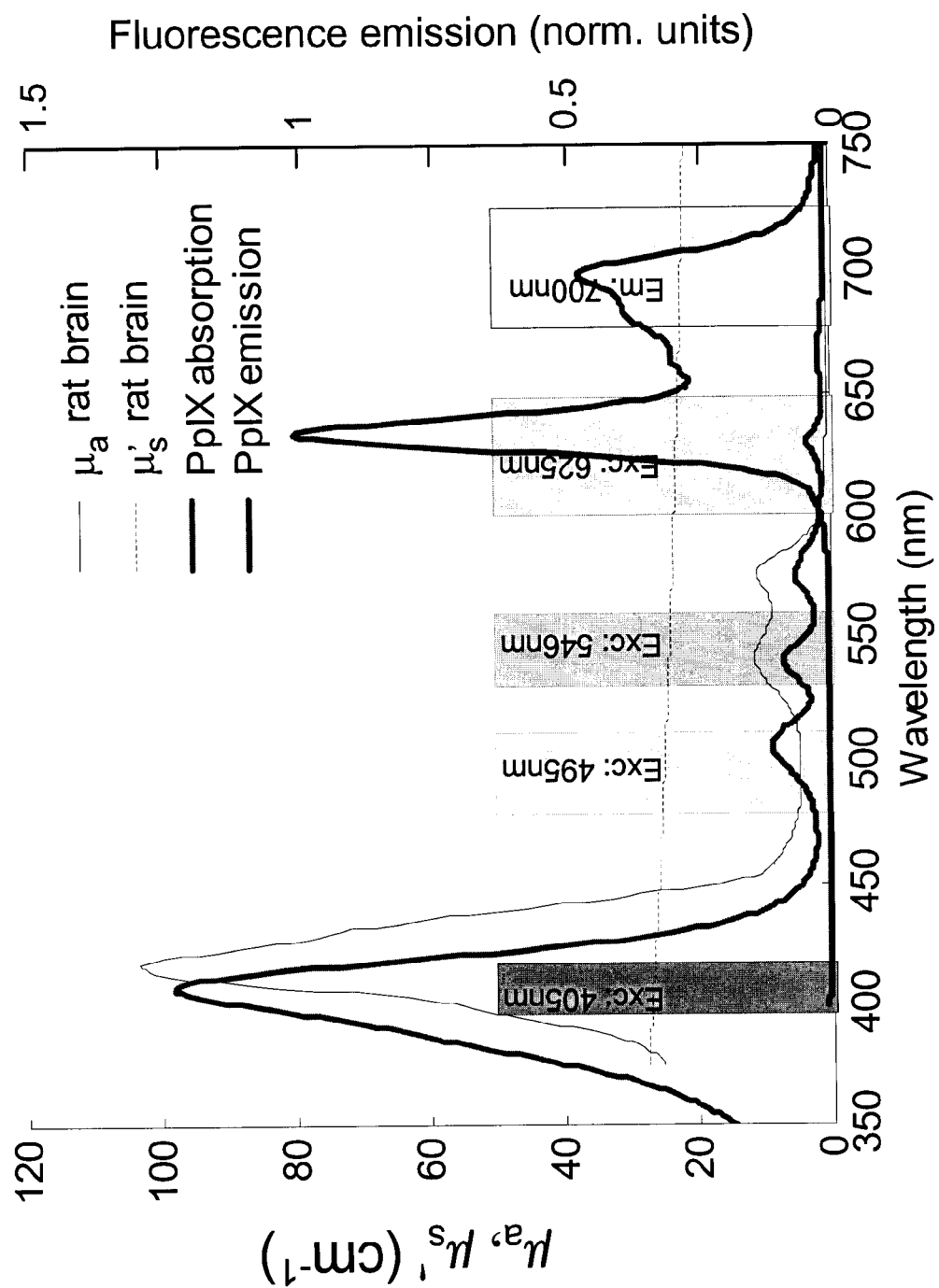
FIG. 6 is a set of graphs showing example absorption and reduced scattering coefficient spectra of rat brain, protoporphyrin IX (PpIX) absorption and emission curves, and excitation and emission filter bands that may be suitable for PpIX.

The optical absorption and transport scattering coefficients, $\mu_a$ and $\mu_s'$ respectively, are inputs into this model. FIG. 6 displays these optical properties according to wavelength, together with the absorption and fluorescence emission spectrum of PpIX (a fluorophore that may be suitable for targeting tumor cells), as well as the excitation and emission bands used for the imaging. FIG. 6 shows the absorption and emission curves for PpIX, and excitation and emission (denoted "Exc" and "Em" in the diagram) filter bands that may be suitable for PpIX.

Figure 7:
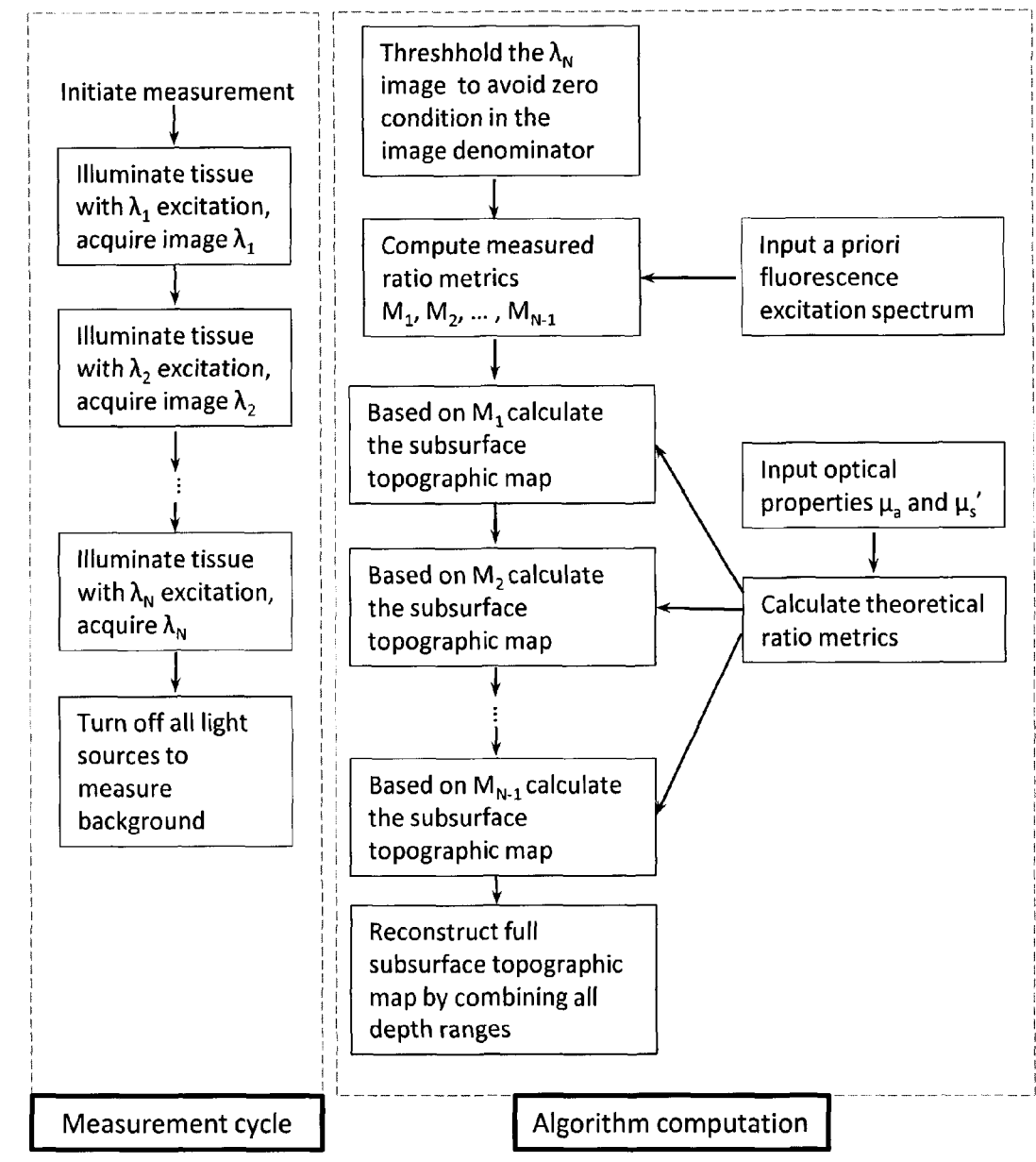
FIG. 7 is a diagram outlining an example method for measurement of fluorescence excitation images and an example algorithm to produce sub-surface fluorescence topographic maps using the ratiometric technique.

FIG. 7 shows a flowchart outlining an example method for measurement of fluorescence excitation images and an example algorithm to produce sub-surface fluorescence topographic maps using the example ratiometric technique described above.

In this example, in the "Measurement cycle" part, the imaging system and computer-controlled excitation light source (e.g. filter wheel coupled to a broadband light source, or LEDs) work in concert to sequentially acquire fluorescence images at different excitation wavelengths. In the "Algorithm computation" part, an algorithm according to the above modeling using the described ratiometric technique is applied.

Figure 8:
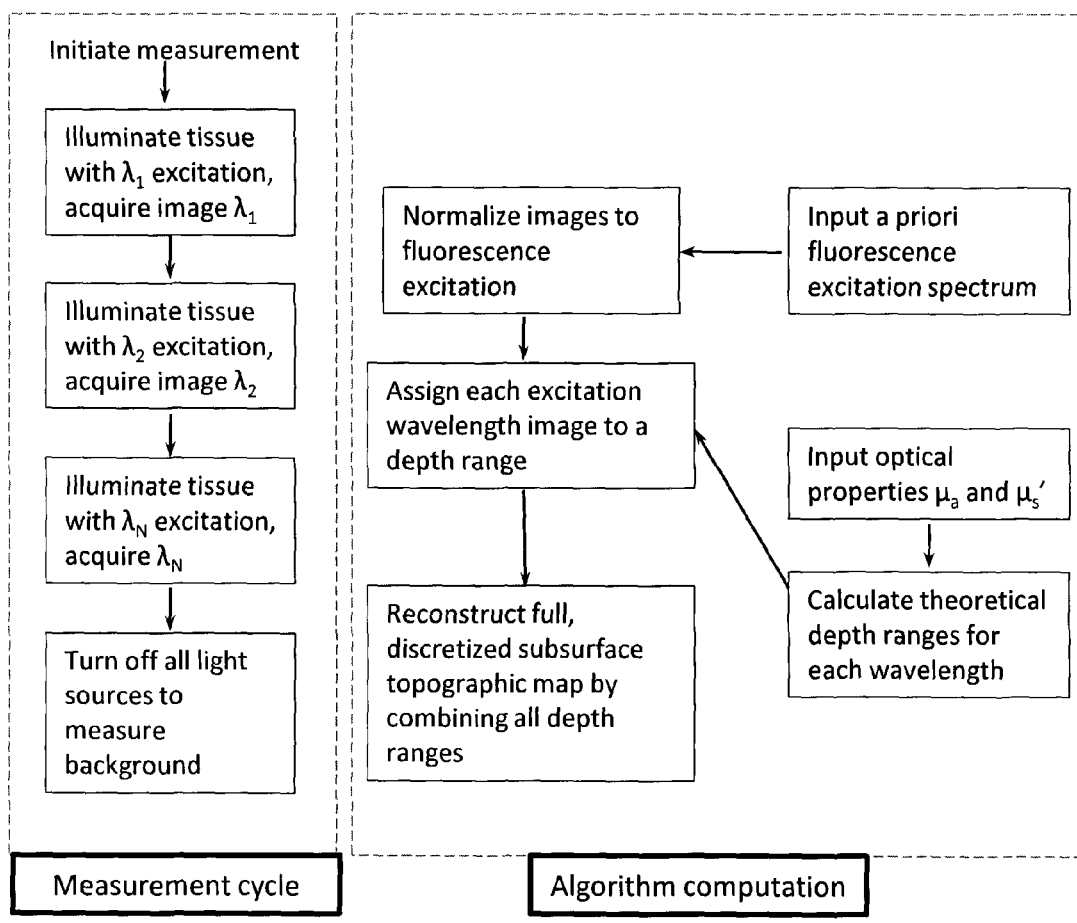
FIG. 8 is a diagram outlining an example method of measurement of fluorescence excitation images and an example algorithm to produce sub-surface fluorescence topographic maps using the discrete range technique.
Figure 9A:
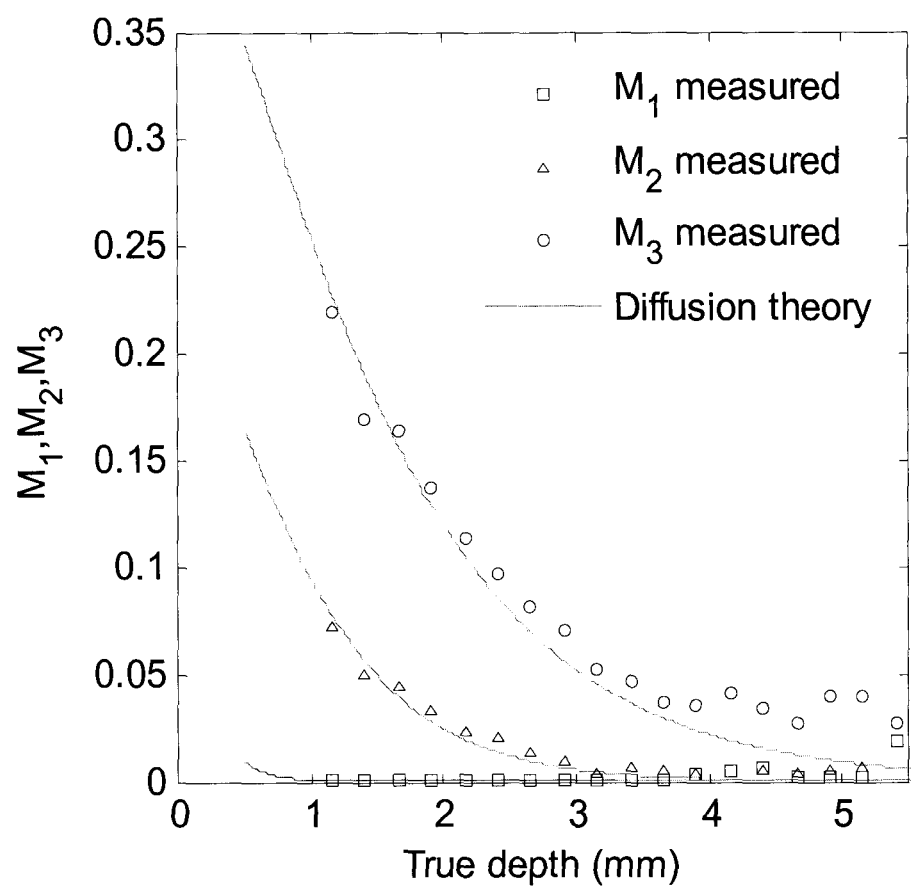
FIG. 9a shows graphs for example ratio metrics for various excitation bands.
Figure 9B:
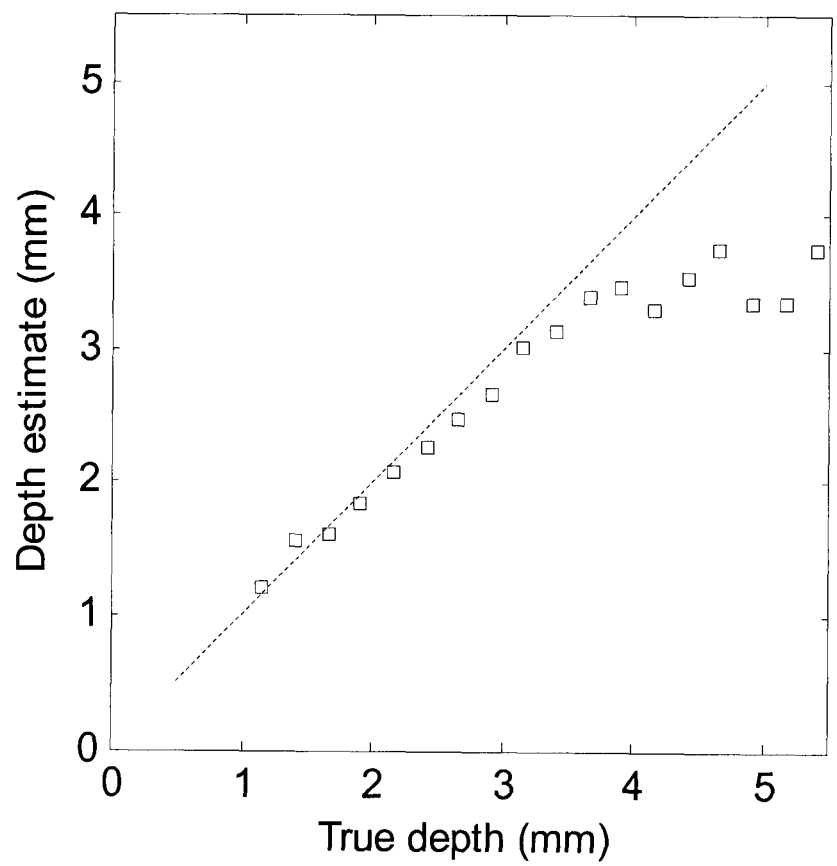
FIG. 9b shows depth estimate from example phantom data plotted against the true depth.
Figure 10A:
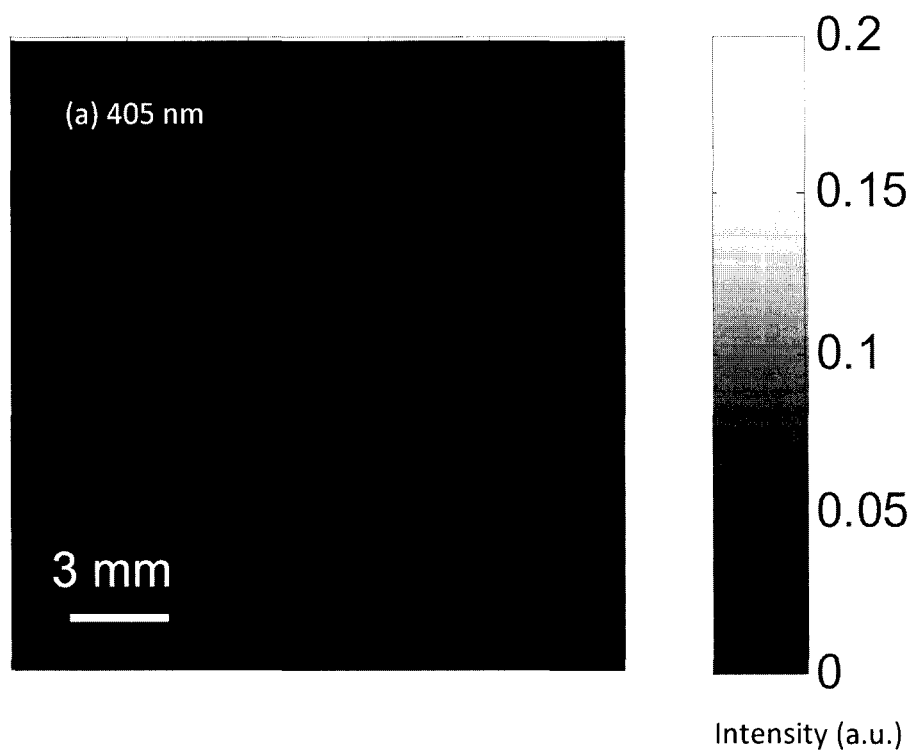
FIGS. 10a-10h show images of an example sub-surface brain tumor imaged in vivo.
Figure 10B:
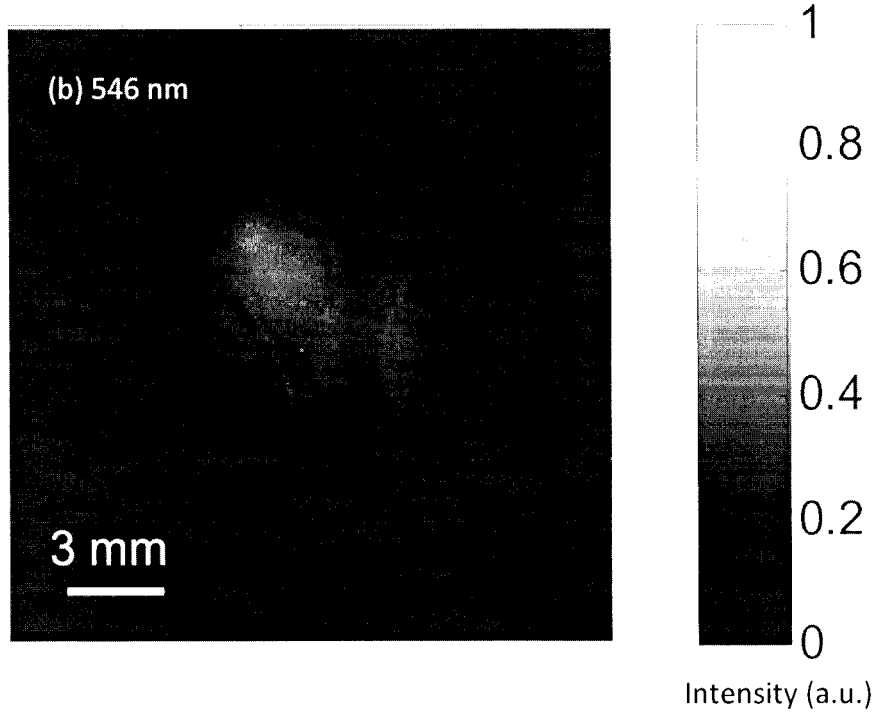
Figure 10C:
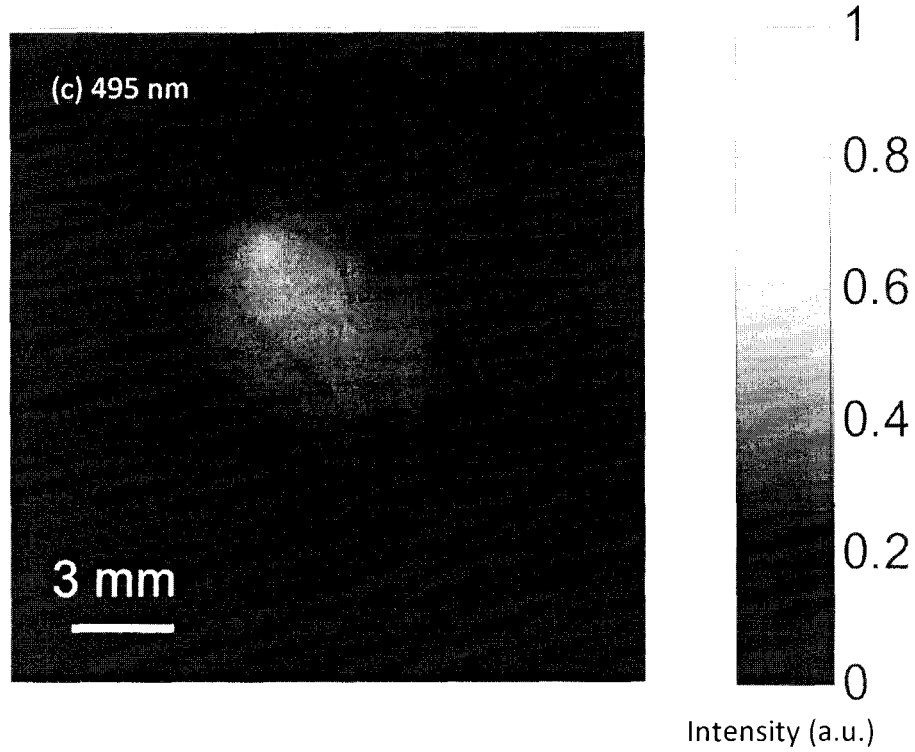
Figure 10D:
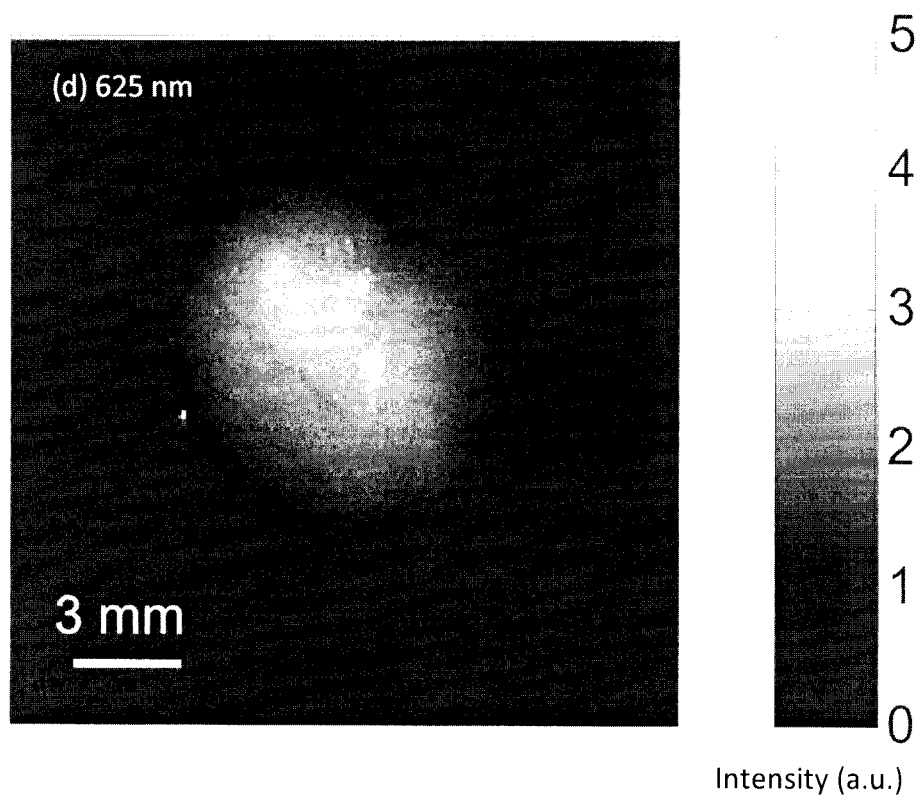
Figure 10E:
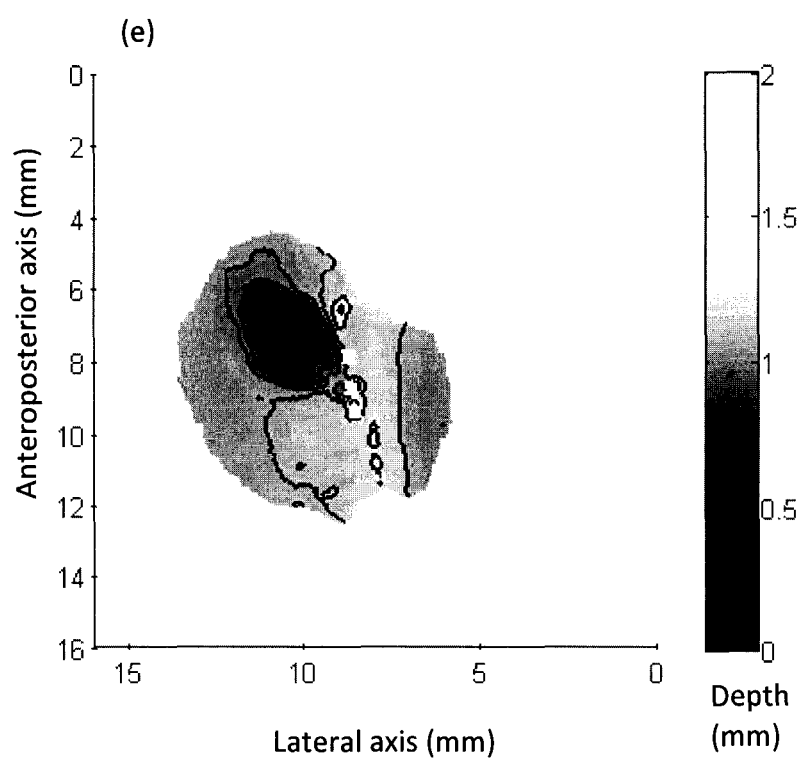
Figure 10F:
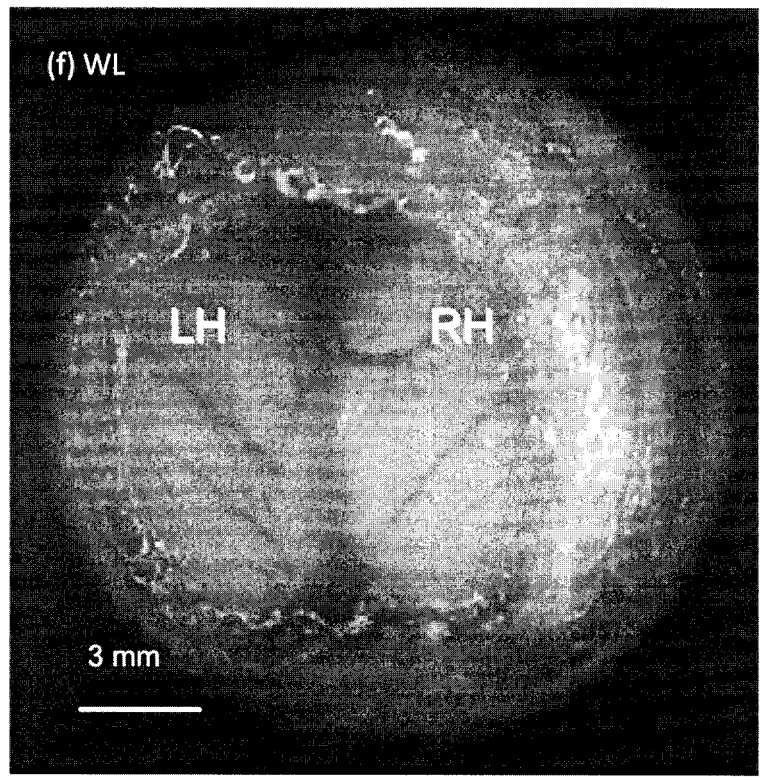
Figure 10G:
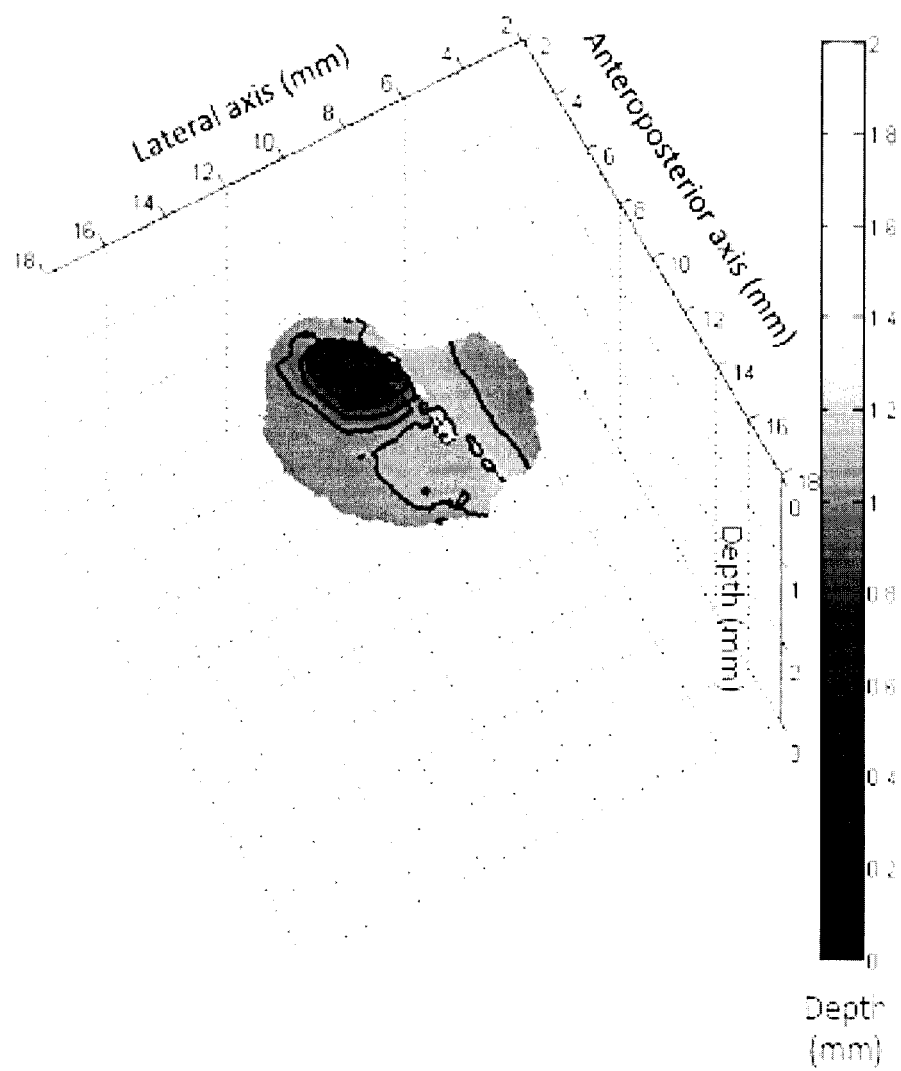
Figure 10H:
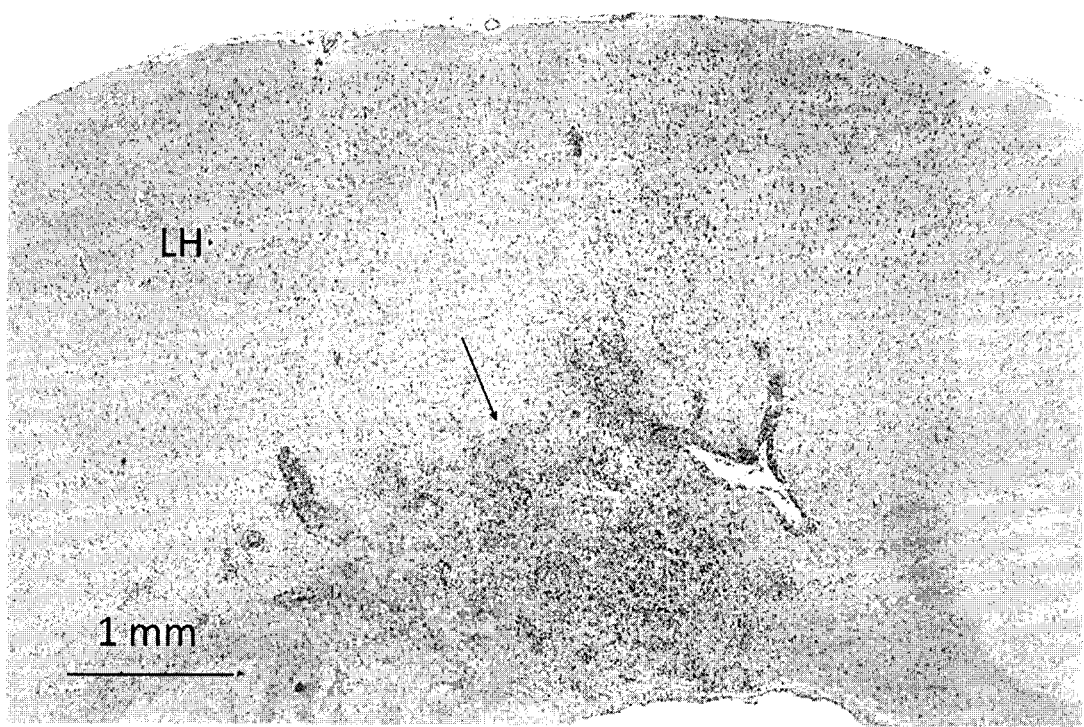
Figure 11A:
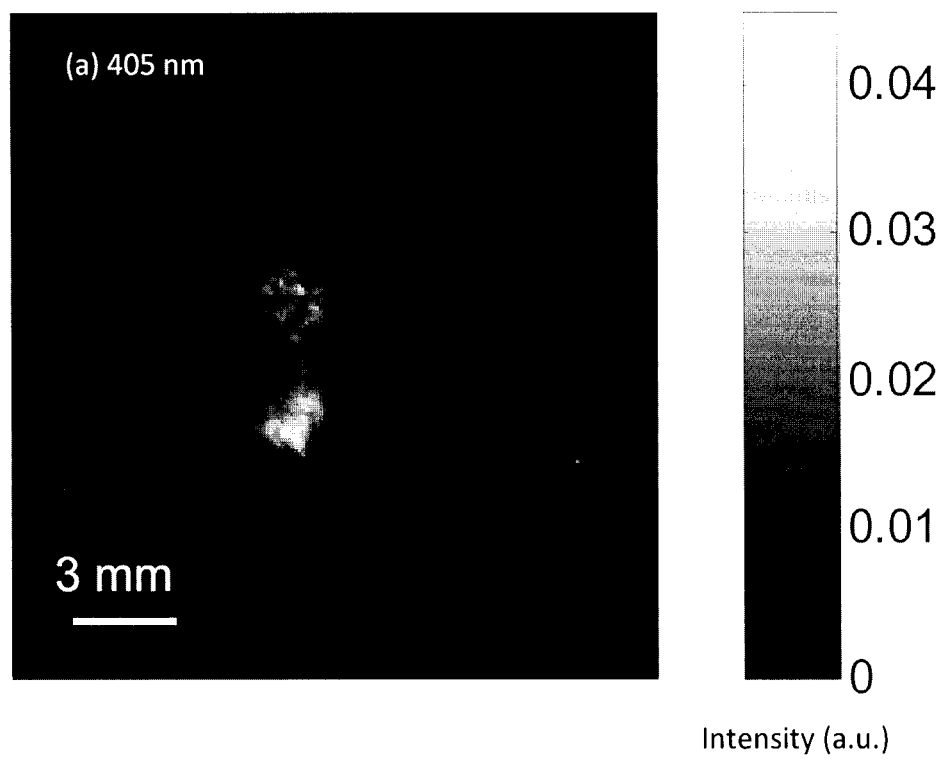
FIGS. 11a-11h show images of another example sub-surface brain tumor imaged in vivo.
Figure 11B:
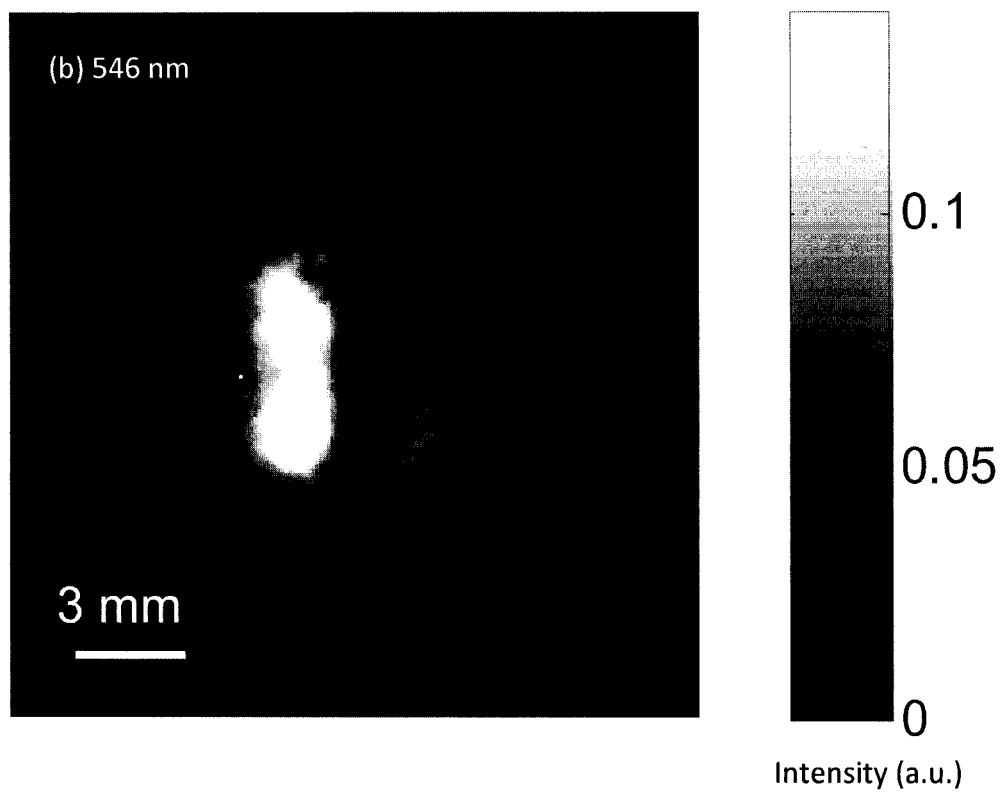
Figure 11C:
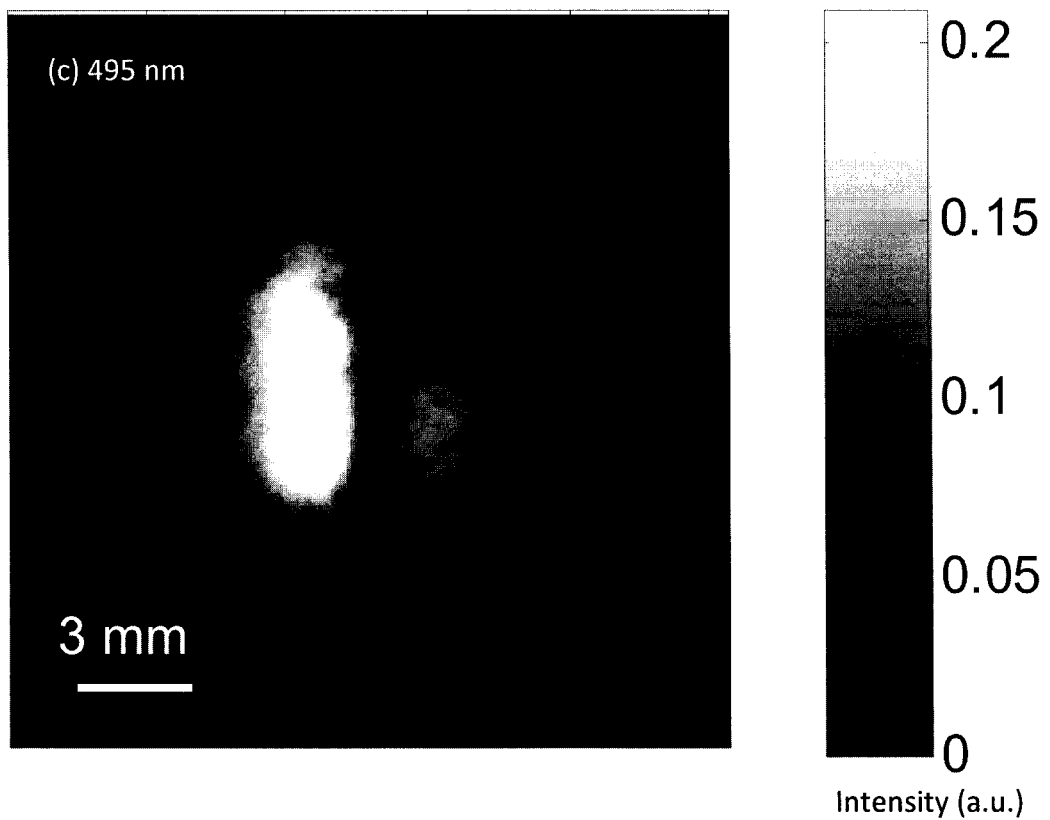
Figure 11D:
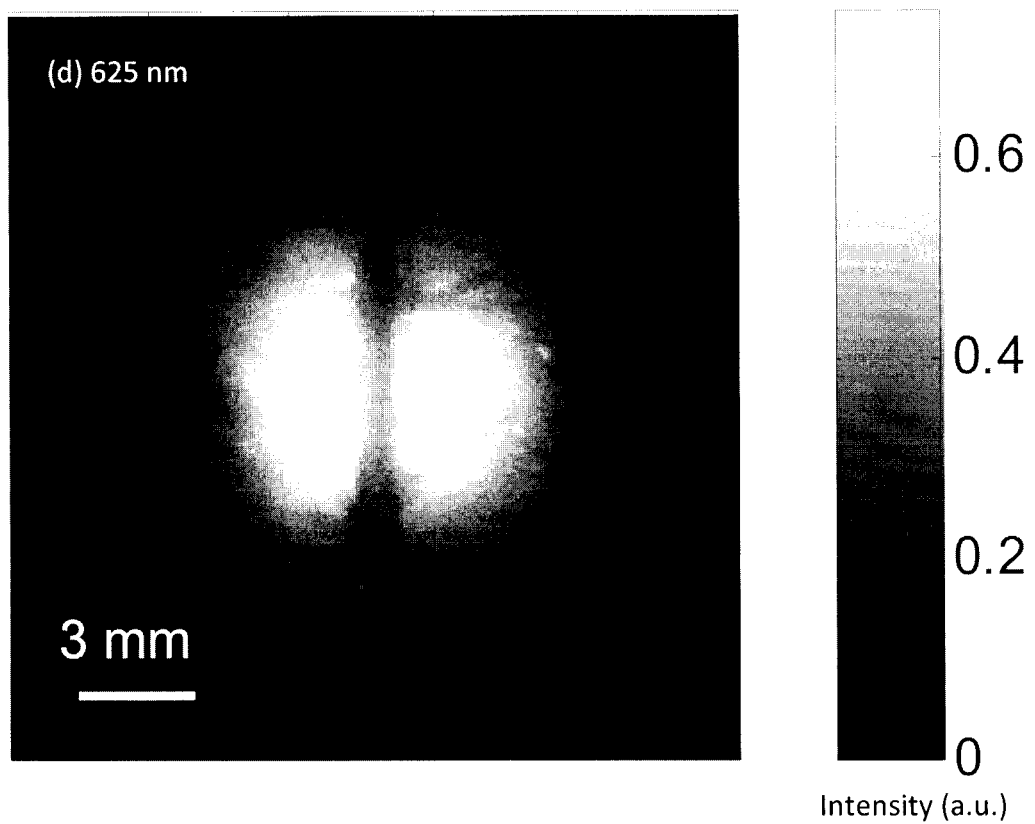
Figure 11E:
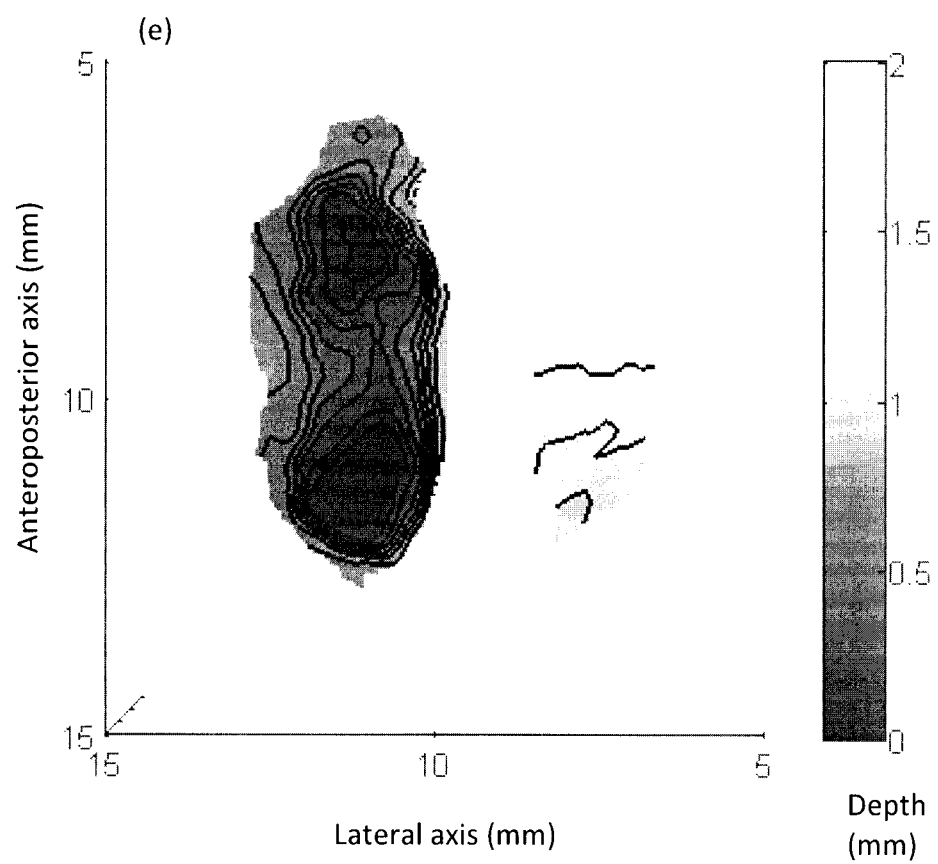
Figure 11F:
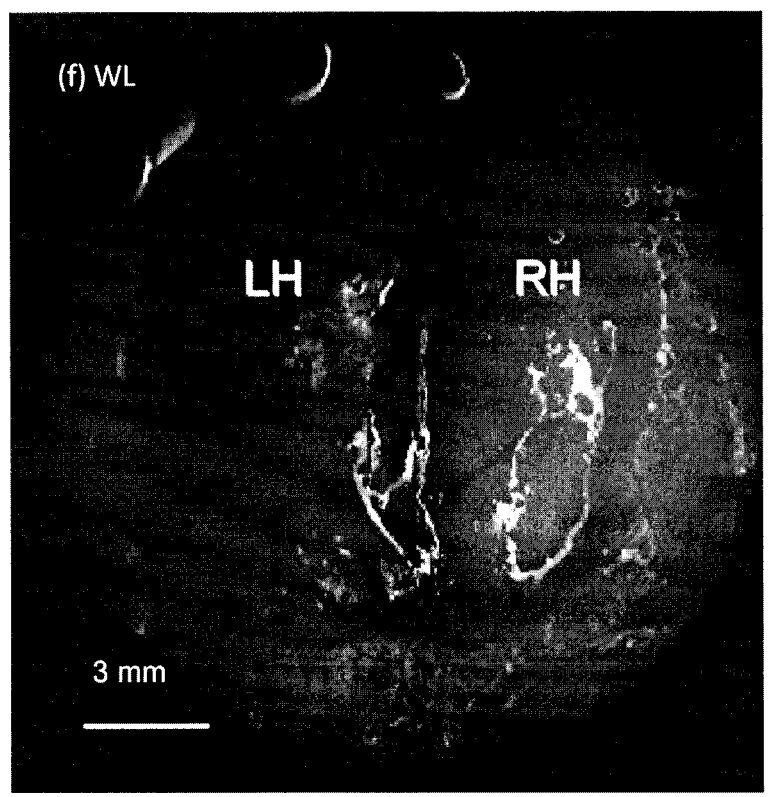
Figure 11G:
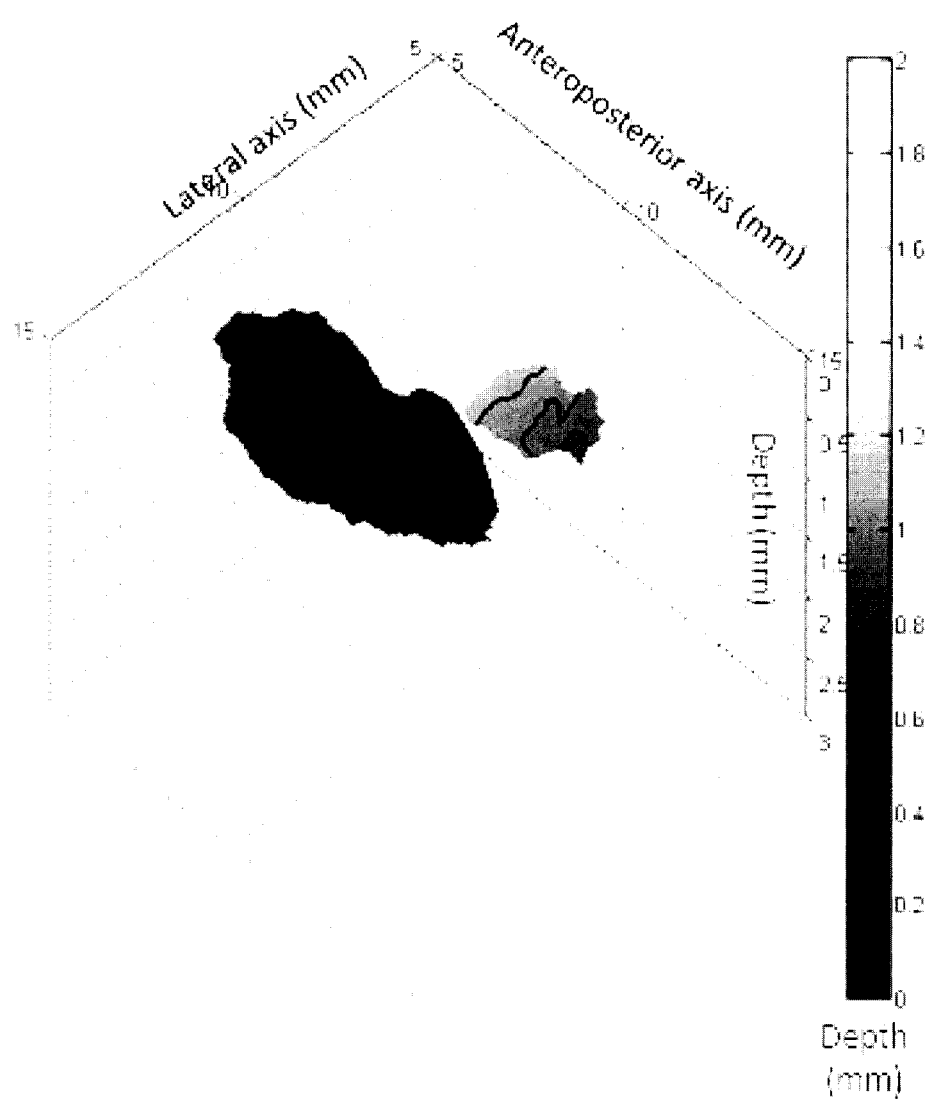
Figure 11H:
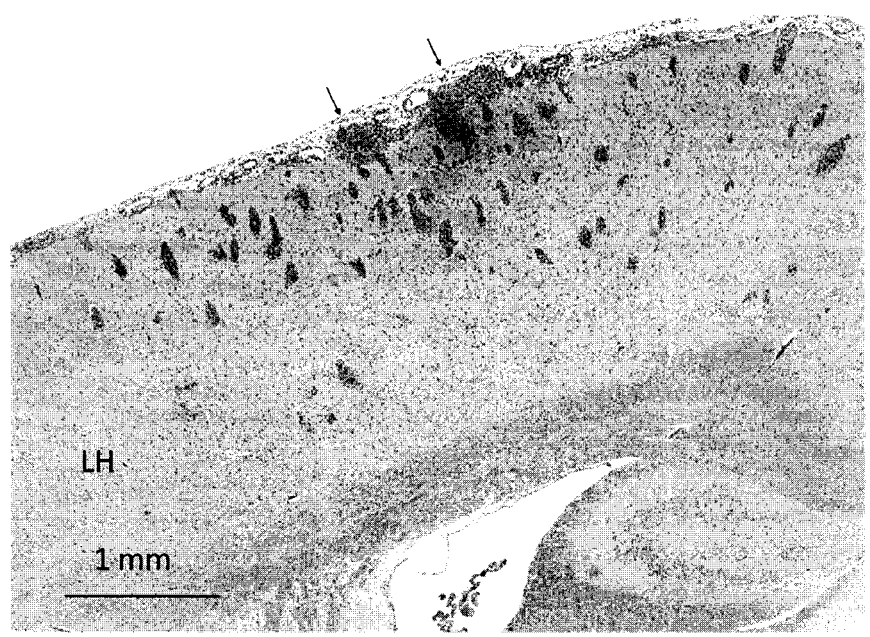

Another example algorithm, alternative to that of the ratiometric technique, is shown in FIG. 8, where each excitation image represents a depth range. This example method is referred to as the discrete range method. FIG. 8 is a diagram outlining an example method of measurement of fluorescence excitation images and also an example algorithm to produce sub-surface fluorescence topographic maps using the discrete range technique.

In order to model the re-emission of fluorescence, the $R_m(r,z)$ term (refer to FIG. 5) is modeled. The approach shown in the following example is to use the diffusion theory equation for spatially-resolved, steady-state diffuse reflectance (Farrell et al., 1992), although other modeling methods may be used (e.g. Monte Carlo or any other suitable methods). In the case of modeling the diffuse reflectance re-emitted from an incident pencil beam, the buried point source would be 1 mfp' (reduced mean free path) deep within the tissue. Here, the buried point source in the tissue is at an arbitrary depth, z, to model an isotropic point emitter:

$$R_m(r,z) = \frac{1}{4\pi}\left[z\left(\mu_{eff,m}+\frac{1}{r_1}\right)\frac{e^{-\mu_{eff,m}r_1}}{r_1^2} + (z+2z_b)\left(\mu_{eff,m}+\frac{1}{r_2}\right)\frac{e^{-\mu_{eff,m}r_2}}{r_2^2}\right], \quad (8)$$

where and $r_1^2=z^2+r^2$ and $r_2^2=(z+2z_b)^2 r^2$. The extrapolated boundary distance is given by $z_b=2\kappa D_m$, where $D_m$ is the diffusion constant at the emission wavelength. The effective attenuation coefficient is $\mu_{eff,m}=\sqrt{3\mu_{a,m}\mu'_{t,m}}$. The internal reflection parameter is given by $\kappa$ $(1+r_{id})/(1-r_{id})$, due to refractive index mismatch between the air and tissue. An empirical model for $r_{id}$ has been derived, where $r_{id}=-1.44n_{rel}^{-2}+0.71n_{rel}^{-1}+0.67+0.0636n_{rel}$ and $n_{rel}=$ $n_{tissue}/n_{air}$ (Groenhuis et al., 1983). Matching internal and external refractive indices yields κ=1. In this example work, $n_{rel}$=1.4.

Figure 12:
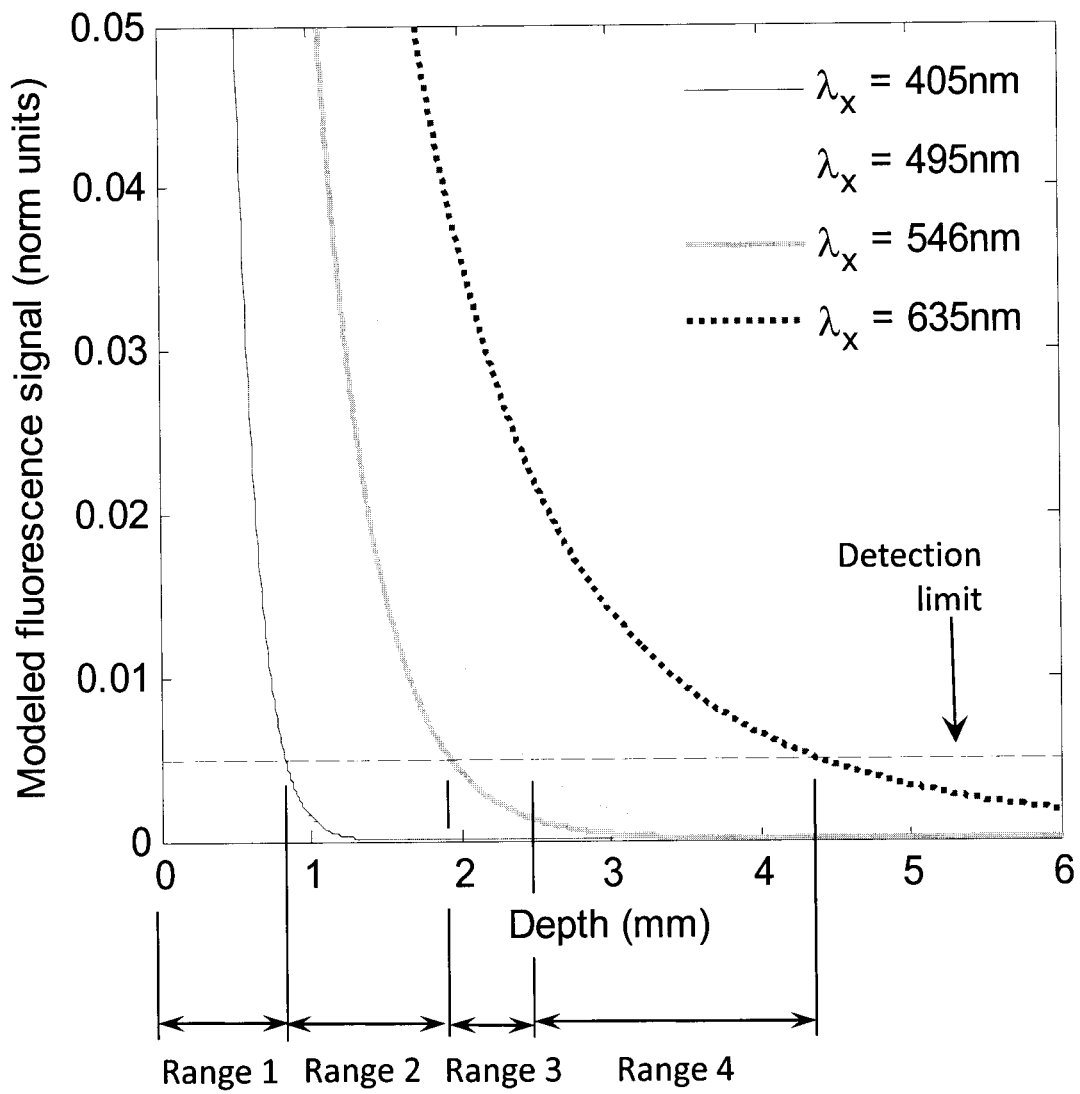
FIG. 12 shows example fluorescence emission curves with respect to depth as calculated from a diffusion theory model of light transport.

Diffusion theory graphs of the fluorescence of a buried object at varying depth are plotted in FIG. 12. FIG. 12 shows example fluorescence emission curves with respect to depth as calculated from a diffusion theory model of light transport. Depth ranges are defined by where each curve intersects a detection limit of a CCD camera. FIG. 12 demonstrates why it is the top surface (i.e., the surface closest to the target surface) of the fluorescing object that is mapped in the sub-surface fluorescence topographic image. The fluorescence intensity of all wavelengths decrease at an exponential-like rate with respect to depth. As a result, fluorescence of the top surface (which may refer to a thin layer corresponding to the top surface, and which may also be referred to as the top surface layer) is the primary contributor to the fluorescence signal. Hence, any algorithm to extract the depth will effectively involve the top surface or top surface layer of the sub-surface fluorescing object.

In the example shown fluorescence resulting from each excitation wavelength exponentially decreases with depth until it is beneath a detection limit, or some other pre-defined limit. The depth penetration range of each excitation wavelength is well defined from 0 mm (i.e., surface) to some maximum depth. A sub-surface fluorescence topographic map of the underlying fluorescent structures can be reconstructed by associating each excitation wavelength with a depth range, thus providing depth resolution. In this reconstruction method, the depth information from the excitation wavelengths with shallowest depth penetration is overlaid (i.e. takes precedence) over the excitation wavelengths with deeper depth penetration. In other words, the precedence of depth information in the reconstructed image goes from the excitation wavelength with the shallowest depth penetration to the deepest. In this way, depth ranges can be associated with each excitation wavelength. In FIG. 12, example excitation wavelengths 405 nm, 546 nm, 495 nm and 625 nm therefore have depth ranges of Range 1=0-0.8 mm, Range 2=0.8-1.9 mm, Range 3=1.9-2.4 mm and Range 4=2.4-4.4 mm.

Since the curves in FIG. 12 decrease approximately exponentially with depth, the ranges do not change significantly even with a two-fold or halving of the fluorophore concentration, with a sufficiently low detection limit. For example, if the fluorophore strength was doubled, the ranges would be at 405 nm, 0-0.93 mm; at 546 nm, 0.93-2.2; at 495 nm, 2.2-2.8 mm; and at 625 nm, 2.8-5.4 mm.

In the example algorithm illustrated by FIG. 8, the fluorescence images are normalized to a fluorescence excitation image prior to application of the depth range estimation algorithm. In this example, the image used for normalization may be a wide-field image of the target fluorophore (not buried, for example, in a Petri dish). This will normalize for the beam shape of the excitation light (for example, the beam shape in the small animal imager of FIG. 4 is Gaussian-shaped) as well as for the camera optics, excitation optical power and fluorophore absorption.

Figure 16:
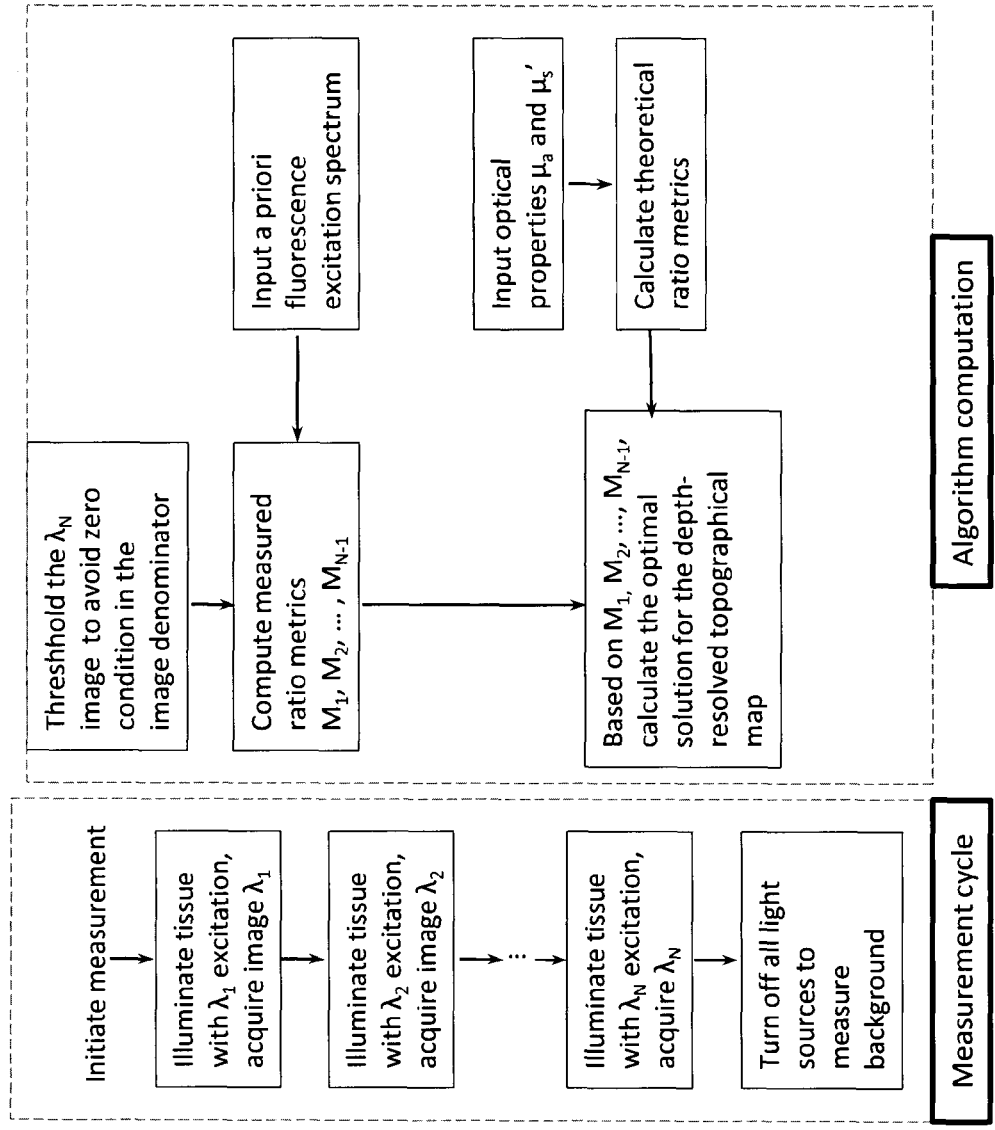
FIG. 16 is a diagram outlining an example method for measurement of fluorescence excitation images and an example algorithm to produce sub-surface fluorescence topographic maps using the ratio metrics in a multi-variable optimization algorithm.

FIG. 16 demonstrates another example algorithm that is similar to that shown in FIG. 7 except that all of the ratio metrics $M_1, M_2, \ldots, M_{N-1}$ are used in combination in an example multi-variable optimization algorithm to calculate the sub-surface fluorescence topographical map.

FIG. 16 is a diagram outlining an example method for measurement of fluorescence excitation images and an example algorithm to produce sub-surface fluorescence topographic maps using the ratio metrics in an example optimization algorithm. This example method may be useful for decreasing any error between the measurements and an appropriate model of the buried fluorescence.

Here, a theoretical model (e.g. diffusion theory, Monte Carlo, or any other suitable model) of the buried fluorescence model (see FIG. 5) is compared with the ratio metrics, and the error between the measurements and model are minimized in an optimization algorithm. In some examples, the image data, rather than the ratiometric data, may be used to perform this calculation.

In another example, further to the algorithms illustrated by FIG. 7, FIG. 8 and FIG. 16, quantitative information on the abundance of fluorophores in the target media may be considered. A distance-ranging tool, such as a laser distance measurement device, which may be provided on the imaging system, may be used to determine the distance between the imaging system and the target surface. Correcting for the inverse dependence between light intensity and camera distance, and taking into account tissue optical attenuation based on the aforementioned light-tissue transport models, it may be possible to incorporate quantitative information on the fluorescence intensity in combination with the depth-resolved data.

In some examples, the method may further include detecting background reflectance of the target surface and taking this into account. This can be achieved by illuminating the target surface with light over a major portion of the detected emission wavelengths or wavelength ranges (e.g., broadband white light), for example, and detecting the resulting reflectance. The white light reflectance image can be used in conjunction with a known signal-to-background ratio to subtract the background from acquired fluorescence images. In some examples, this background subtraction can be performed using any suitable method, for example directly to the raw image data, or during or after post-processing computation, such as that described above.

Example Study

In an example, the validity of the example ratiometric model described above was tested first in a tissue-simulating phantom. A 1 mm inner diameter capillary tube was filled with PpIX (Sigma-Aldrich, Oakville, ON, Canada) in dimethyl sulfoxide (DMSO). A liquid phantom was formulated with Intralipid (Fresenius Kabi, Germany) to model tissue scattering, rodent blood to typically 10 s. Subsequently, after sacrifice by anesthetic overdose, the brain was removed intact, fixed in formalin and coronal H&E histology sections were taken.

FIG. 10 and FIG. 11 show two examples of the results, in the first of which the tumor was fully sub-surface, while in the second it was largely located on the cortical surface.

FIG. 10 shows images of an example sub-surface brain tumor imaged in vivo: a-d) individual fluorescence images at each excitation wavelength. The color bars indicate the relative fluorescence intensity (arbitrary units); e) sub-surface fluorescence topography image; f) white light image; g) sub-surface fluorescence topography in isometric view; h) coronal H&E histology with the arrow showing the top surface of the sub-surface bulk tumor (i.e., the surface facing towards and closest to the target surface).

FIG. 11 shows images of an example brain tumor located on the cortical surface imaged in vivo: a-d) individual fluorescence images at each excitation wavelength. The color bars indicate the relative fluorescence intensity (arbitrary units); e) sub-surface fluorescence topography image; f) white light image; g) sub-surface fluorescence topography in isometric view; h) coronal H&E histology with the arrow showing the top surface of the sub-surface bulk tumor (i.e., the surface facing towards and closest to the target surface).

The individual spectral images show the increasing light penetration with wavelength, as the tissue absorption and scattering decrease. Using the above example model, depth-resolved topographic images were derived and are shown in FIG. 10 and FIG. 11, for example, with the corresponding white light images in panel f. The corresponding H&E-stained histology sections illustrate the location of the tumors relative to the brain target surface.

These example studies illustrate the feasibility of this technique, in a small-rodent brain tumor model, and show that, using PpIX, one could expect to detect and localized fluorescence at least up to ~3 mm below normal brain surface. In order to achieve greater imaging depth, it may be useful to use a fluorophore with high fluorescence quantum yield and/or excitation and emission in the far red to near-infrared wavelength ranges, of which several are under development or commercially available.

Applications

Although the above examples describe the use of the disclosed method and system for imaging of brain tumors, there may be other suitable biomedical applications for the disclosed sub-surface fluorescence topography. For example, during surgery, it is useful to limit damage to large blood vessels. In such an example application, blood vessels may be marked using an appropriate fluorescent agent, such as indocyanine green (ICG), which may be injected intravascularly. It may also be possible to use a fluorescent contrast agent that specifically targets certain tissues, for example the endothelial lining of blood vessels, such as a fluorescent agent conjugated to a monoclonal antibody that reacts with CD31, a membrane glycoprotein that is important in angiogenesis. By providing a way to localize the depth and spatial location of buried blood vessels, the present disclosure may be useful in surgery, for avoiding cutting into blood vessels and limiting the amount of blood loss.

Another example application may be a use of the disclosed method and system during organ transplant surgery. For example, it may be useful to confirm that blood flow is reaching deep within the organ once the surgeon attaches the patient blood supply to the transplanted organ. One conventional technique is to use indocyanine green injections to confirm using fluorescence imaging that blood is flowing through the blood vessels in the organ. The disclosed method and system can be used to create a depth-resolved map of the vasculature network to ensure that blood flow has been achieved over a large depth range.

In another example application, dermatology may benefit from depth-determination of sub-surface blood vessels under the skin, given a vascular fluorescent contrast agent. For example, laser ablation of birthmarks (e.g., port-wine stains) typically requires depth information of the sub-surface blood vessels for successful treatment planning. Similarly, enhanced treatment planning regimens based on blood vessel depth information may be useful for laser therapy of spider veins, varicose veins and rosacea.

In another example application, the disclosed method and system may also be used for small animal imaging of in situ tumors during preclinical research, for example as an adjunct or a low-cost alternative to fluorescence tomography.

In general, the disclosed system and method for topographic imaging of sub-surface fluorescent structures could be applied to a range of different applications, including for example, determination of sub-surface blood vessels during surgery, determining the depth of dermatological vascular lesions to help target laser therapies, non-destructive testing of non-biological materials, encryption of documents, and other biological and non-biological applications.

Example Variations

Figure 13:
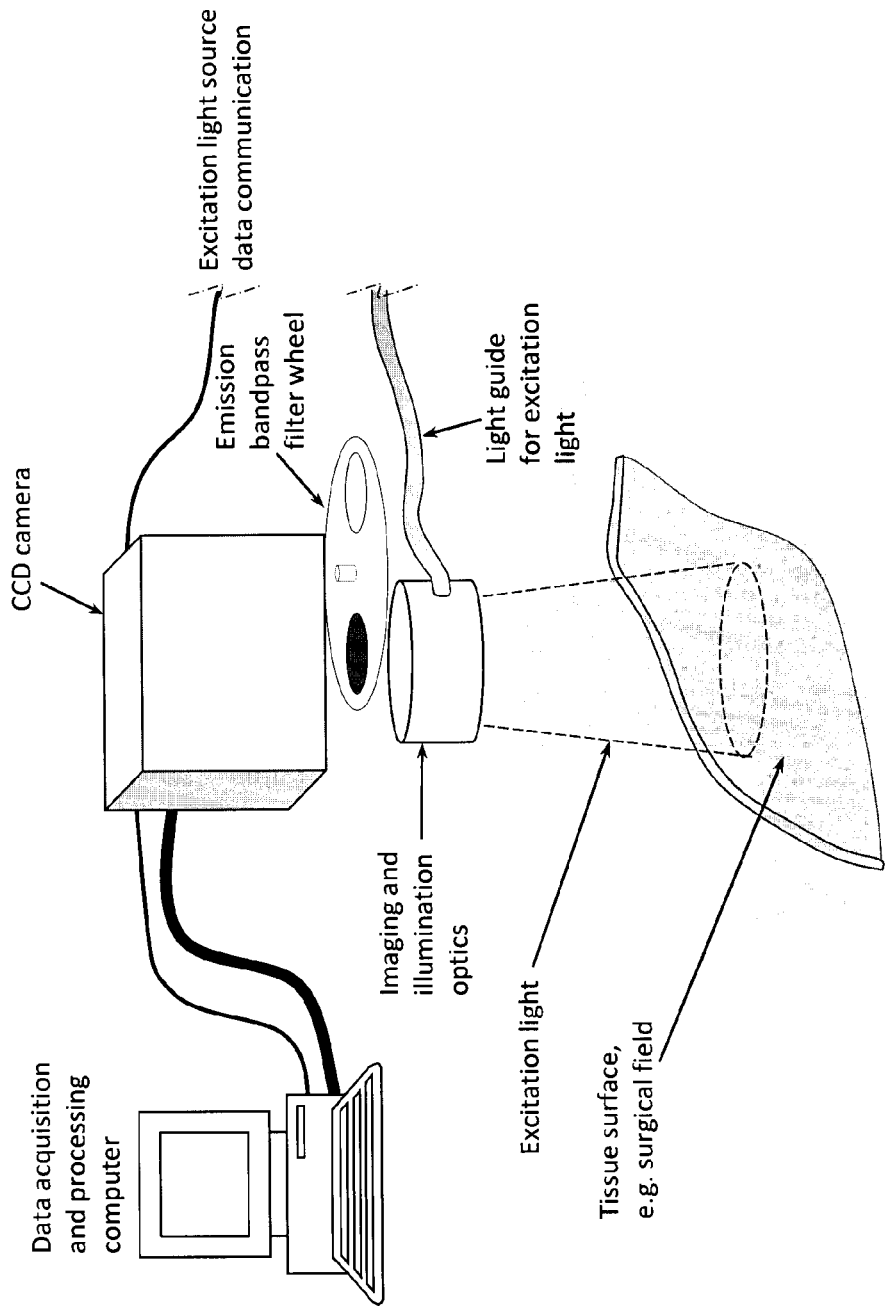
FIG. 13 is a schematic of another example imaging system that may be used to produce multispectral excitation images.

FIG. 13 demonstrates an example variation to the system described above (e.g., in FIG. 1 and FIG. 2) by introducing an emission bandpass filter wheel into the imaging light path (e.g., by including the bandpass filter wheel as a detection filter for the light detector), rather than a fixed emission bandpass filter.

In some examples, the light detector may include a selectable emission filter, which may be automatically selectable (e.g., through computer control) or manually selectable (e.g., through mechanical means). The selectable emission filter may allow for the selectable detection of different emission wavelengths or wavelength ranges, without having to change the entire detection filter. It may be useful to selectably detect different emission wavelengths or wavelength ranges in order to detect emission from different biomarkers (e.g., fluorophores) having different emission wavelengths or wavelength ranges. Examples of suitable selectable emission filters may include a bandpass filter wheel (e.g., computer-controlled filter wheel), an acoutso-optic tunable filter or a liquid crystal tunable filter, among others.

Figure 14:
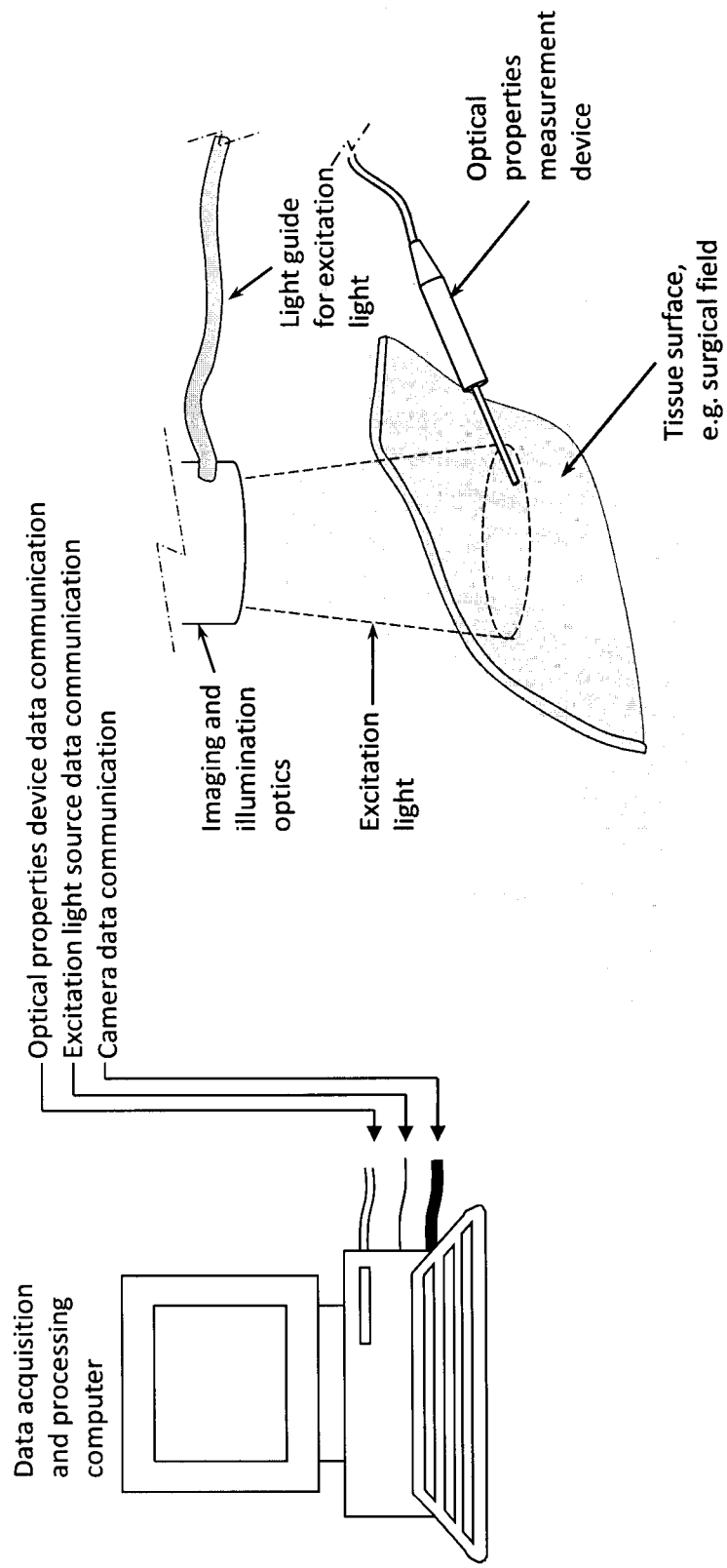
FIG. 14 is a schematic of an example optical properties measurement device suitable for use with an imaging system.
Figure 15:
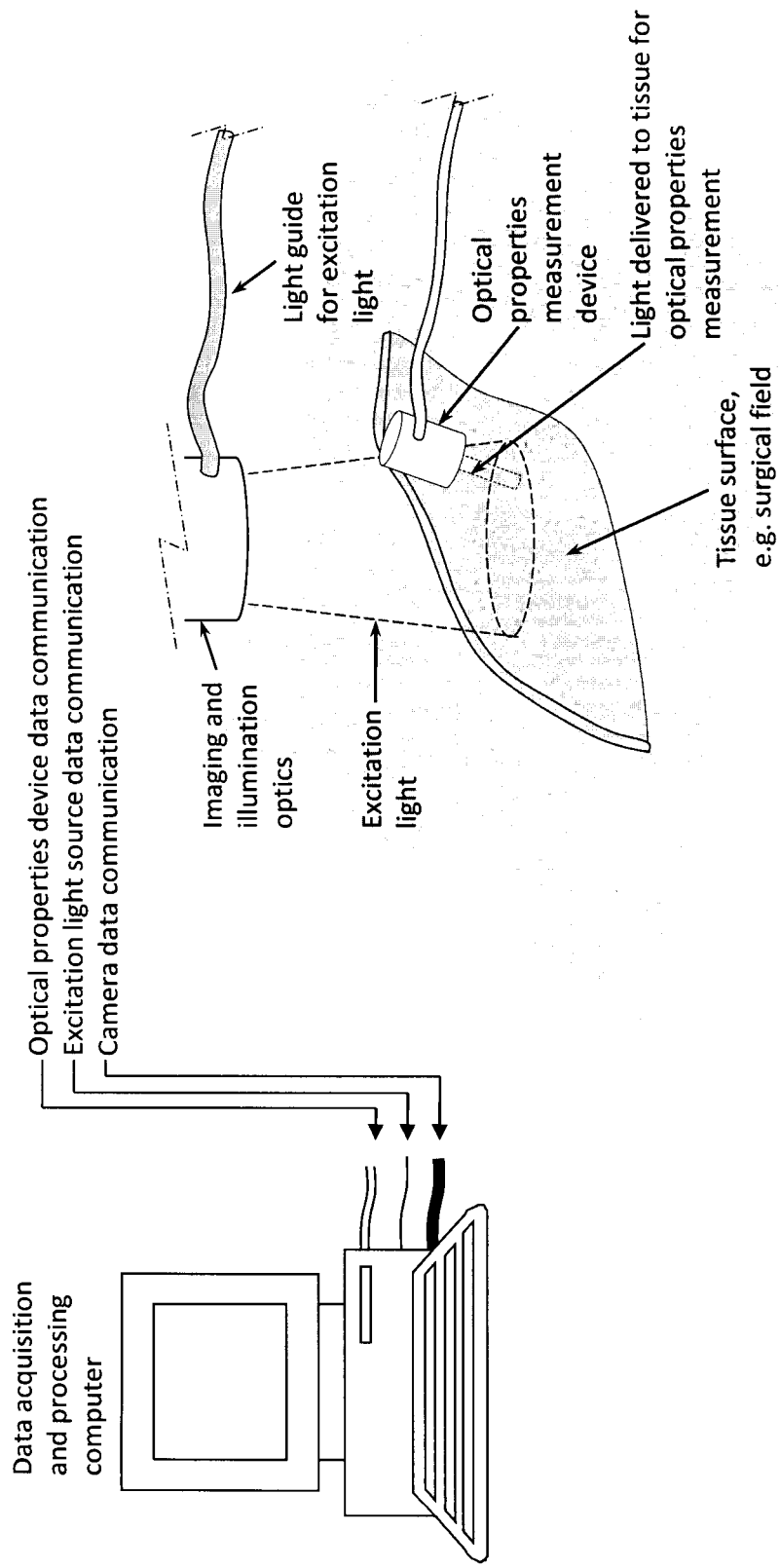
FIG. 15 is a schematic of an example non-contact optical properties measurement device suitable for use with an imaging system.

FIG. 14 and FIG. 15 demonstrate another example variation to the system described above by adding an optical properties measurement device that communicates its data to the data acquisition and processing computer.

FIG. 14 is a schematic of an example optical properties measurement device suitable for use with the imaging system described above, which may be used in the field of view of the imaging system. The example measurement device measures the optical properties by probing the target surface via direct contact. FIG. 15 shows an example optical properties measurement device suitable for use with the imaging system described above. FIG. 15 shows an example non-contact probe that is positioned above the target surface.

Recall from FIGS. 7 and 8 that the optical properties are required for the depth calculations. Rather than have the optical properties required a priori, the optical properties measurement device, for example as shown in FIG. 14 and FIG. 15, can directly provide this data a posteriori, which may help improve the accuracy of the calculation of the sub-surface fluorescence topography. The contact and non-contact optical properties measurement devices each may operate based on any suitable technique such as, for example, total steady-state diffuse reflectance, spatially-resolved steady-state diffuse reflectance, spectrally-constrained steady-state diffuse reflectance, time-resolved diffuse reflectance, frequency-domain diffuse reflectance, spatially-modulated steady-state diffuse reflectance, diffuse optical tomography, pulsed photothermal radiometry, photoacoustic spectroscopy, or any other suitable technique.

Figure 17:
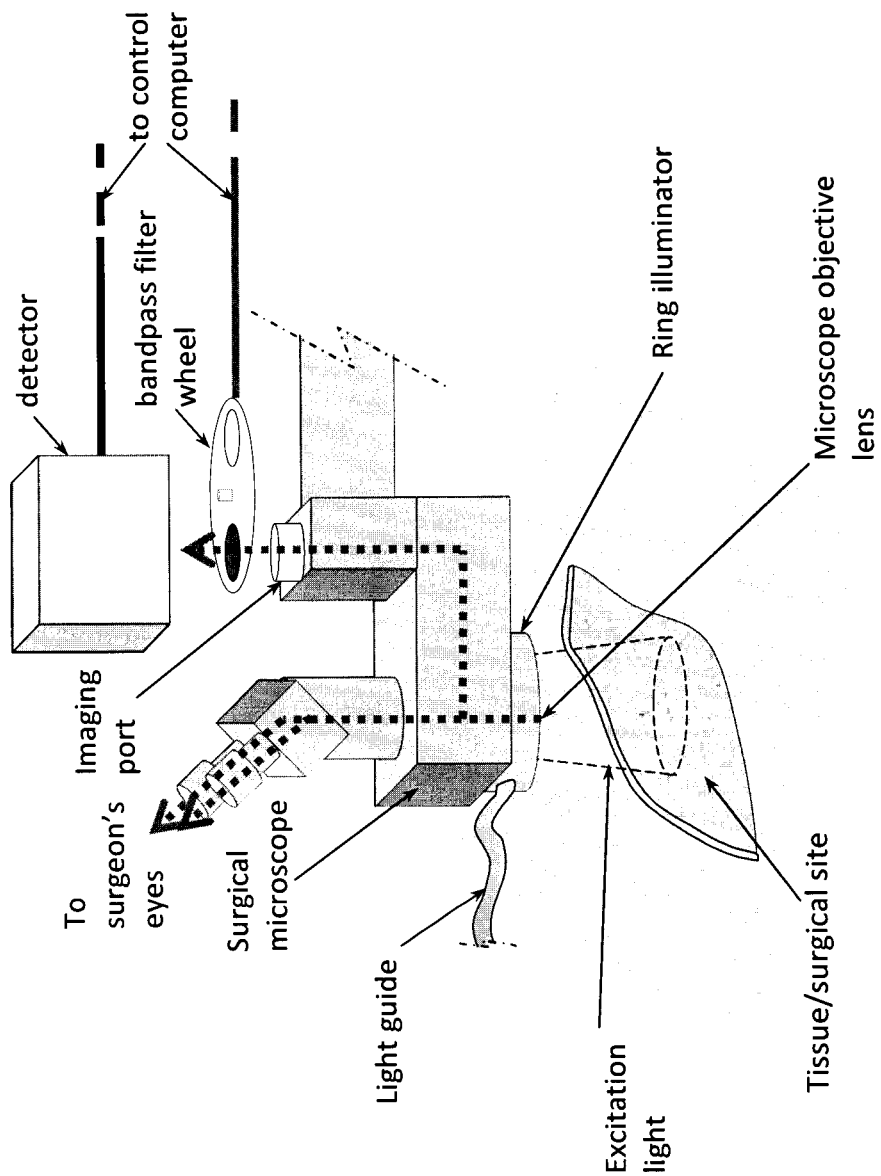
FIG. 17 is a schematic of an example imaging system that may be used to produce multispectral excitation images, implemented in a surgical microscope.

Another example imaging system is shown in FIG. 17, which may be similar to the systems of FIG. 1, FIG. 2 and FIG. 13, with the exception that the imaging system may be incorporated or implemented into the design of a surgical microscope. Use of the imaging system in a surgical microscope may be useful, for example, in surgical procedures where detection of certain sub-surface tissues is desired. For example, such a system may be useful in neurosurgery for detection of sub-surface brain tumor tissue or for determination of the location of sub-surface blood vessels during surgery.

In FIG. 17, thick dotted lines indicate the imaging detection paths of detected light from the target tissue to the detector and to the viewing lens (e.g., for viewing by a surgeon). In this example, the surgical microscope may be supported over the target tissue (e.g., a surgical site), for example by a gantry. The conventional (i.e., unmodified) operation of the surgical microscope typically is to illuminate the tissue surface with (typically) white light from a light source internal to the microscope; collect the reflected light from the tissue into the objective lens of the microscope; then channel and focus the light in such a way to form a magnified image that may be seen through the binocular lens of the microscope that the surgeon may look through. Conventionally, such surgical microscopes typically have additional light paths split off from the binocular light path in order to record images (e.g., using a CCD camera and any suitable focusing optics) for further analysis or other future use. In the example of FIG. 17, an example of the disclosed imaging system may be implemented in a surgical microscope, for example using modifications such as: 1) the addition of multi-spectral excitation illumination; and 2) addition of an imaging/detection system for collecting the fluorescence light.

In this example, illuminating the tissue surface with multi-spectral excitation light may be achieved by channeling a light guide from an external multi-spectral light source to a ring-illuminator (which may be attached to the light guide and the surgical microscope) that is collinear with the microscope objective lens. The additional detection/imaging system may be built upon an existing imaging port (such as a port intended for an external imaging/viewing device, as in the example of FIG. 17), or by engineering a beam splitter in the detection path to create an additional imaging path. In this example, prior to being imaged by a detector (e.g., a CCD camera), the light may be passed through an emission bandpass filter to reject the excitation light, similar to the setup of FIGS. 1, 2 and 13, for example. The emission bandpass filter may be one of multiple emission filters mounted on a filter wheel, as in FIG. 13, for example. The multi-spectral excitation light sequentially illuminates the tissue with different wavelengths or wavelength ranges of light (e.g., via computer control, as in the example of FIG. 1). At each illumination by each excitation wavelength or wavelength range, the detector (e.g., the CCD camera) may acquire an image, and the timing of excitation wavelength or wavelength range change and image acquisition may be controlled by a computer, for example.

The implementation into a surgical microscope, for example as described above, may be useful in that the surgical microscope may be typically used over the same target for the entire surgical procedure. This may allow the microscope to be relatively easily switched from "normal" or conventional operating mode to a different mode that allows for sub-surface fluorescence topographic imaging, without having to switch out equipment.

Figure 18:
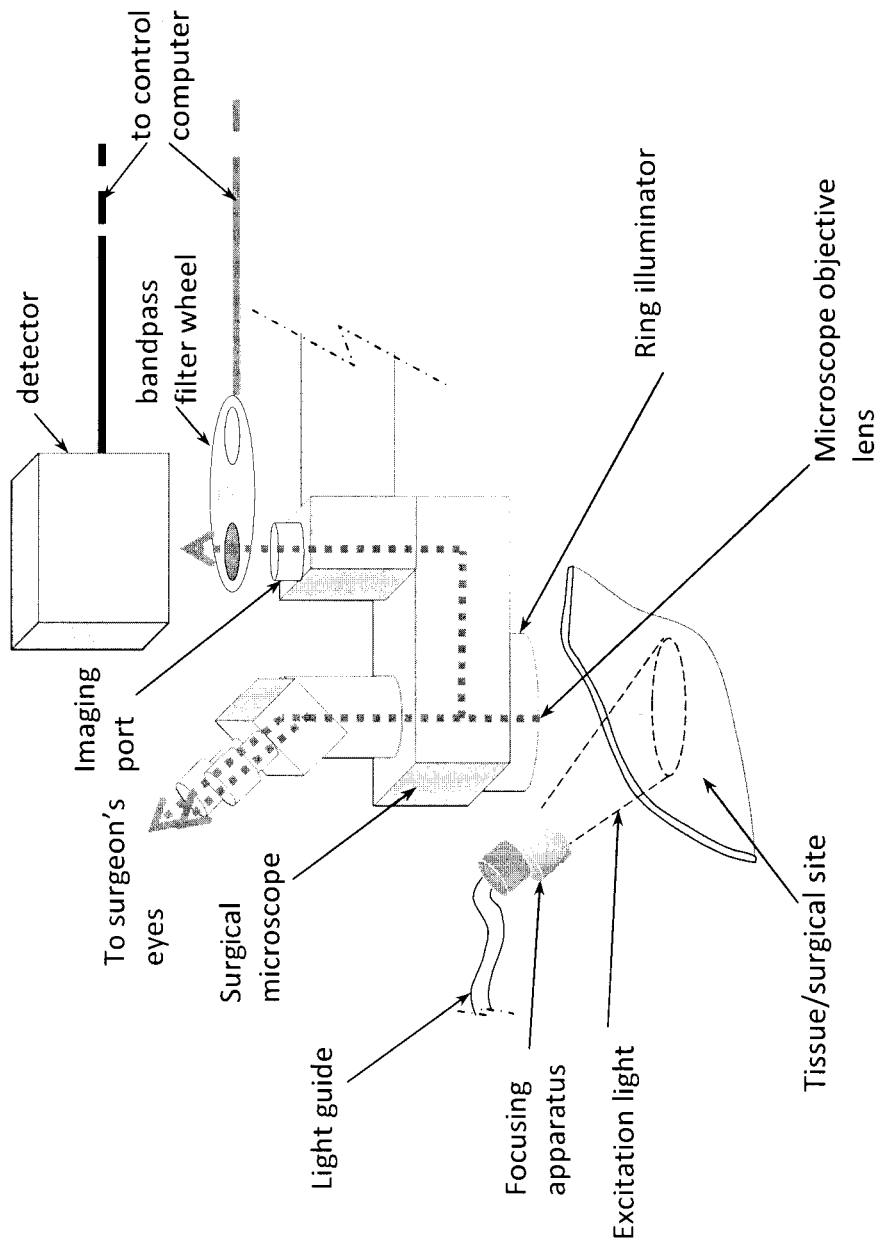
FIG. 18 is a schematic of another example imaging system that may be used to produce multispectral excitation images, implemented in a surgical microscope.

FIG. 18 illustrates another example imaging system implemented in a surgical microscope. The thick dotted lines indicate the imaging detection path of the detected light from the target tissue to the detector and to the viewing lens. The example system of FIG. 18 is similar to that of FIG. 17, with the difference that in the system of FIG. 18, the multi-spectral excitation light is focused from a light guide onto the target tissue via a focusing apparatus (e.g., one or more lenses). The focusing apparatus may be used to adjust (e.g., manually using a focusing knob or lever; or automatically by computer-controlled lens positioning) the beam spot size onto the tissue. The focusing apparatus may also be used to guide the placement of the illumination beam on the target tissue. This may be useful where greater light intensity is desired for a smaller target area, or where a greater target area is desired with lower light intensity, for example.

Figure 19:
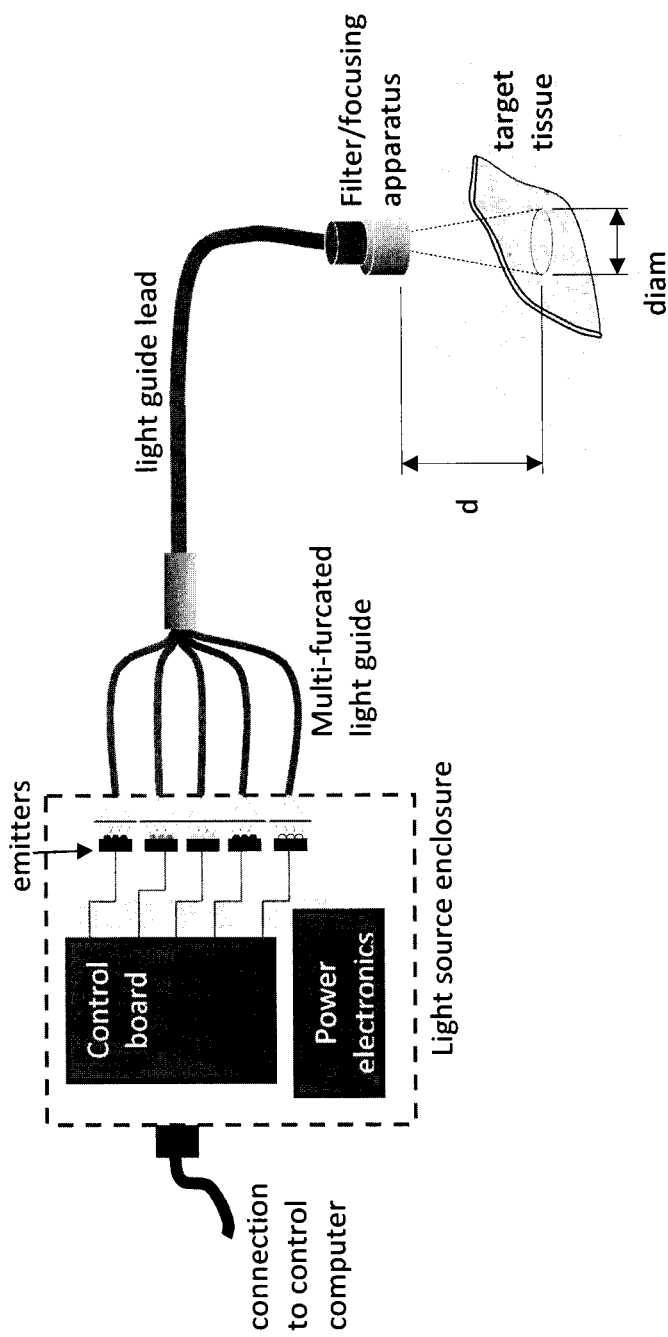
FIGS. 19a-c show an example light source suitable for use in an example imaging system.
Figure 19:
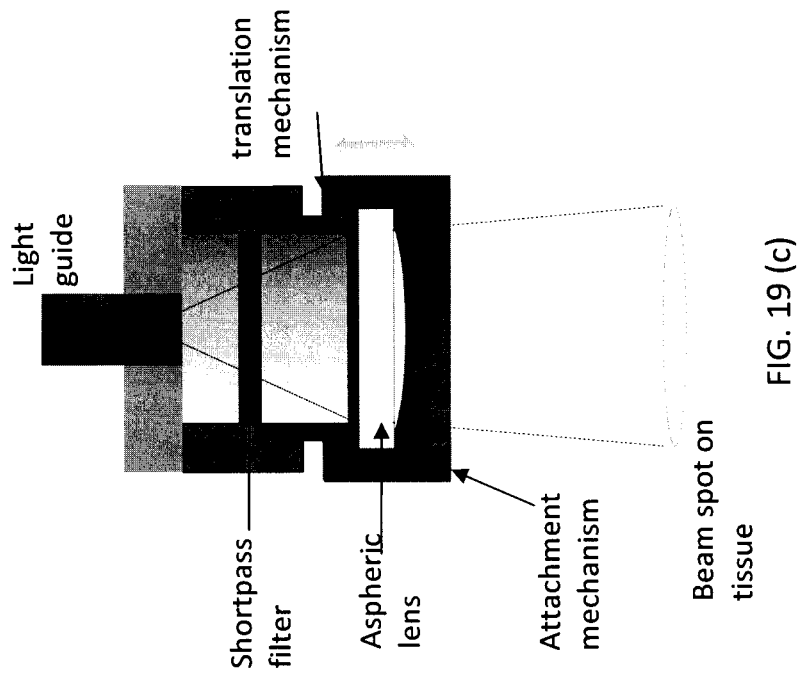
Figure 19:
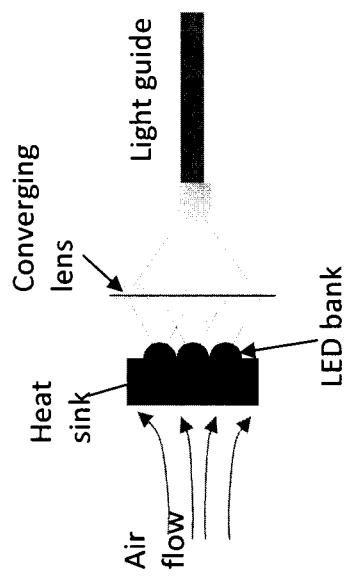

FIGS. 19a-c illustrate an example light source suitable for providing the multi-spectral excitation light for one or more of the imaging systems described above. The example light source of FIGS. 19a-c may include a light source enclosure, and may include multiple components within the enclosure. As shown, the enclosure may include a control board and power electronics for controlling and powering emitters. Cooling fans may be included to cool the components as appropriate. The light source may include a connection (e.g., a USB connection) to a controller, such as a computer. In this example, light from emitters (e.g., LEDs) may be focused (e.g., using suitable optics devices, such as a converging lens as shown in FIG. 19b) onto the furcated ends of a multi-furcated light guide (e.g., a 3m long light guide). A controller (e.g., the control board under control by a processor) may selectably switch individual emitters on or off (e.g., sequentially, synchronized with detection by the detector), such that the light emitted from the end of the light guide (e.g., via a focusing apparatus, such as the example of FIG. 19c) may selectively emit light at different desired wavelengths or wavelength ranges.

In this example, the filter/focusing apparatus may be positioned to illuminate the target tissue at a distance (d) of about 20-25 cm, and may be configured to provide an illumination beam having a diameter (diam) of about 2-4 cm on the target tissue. The distance (d) and/or the diameter (diam) of the beam may be adjustable.

The light guide may be any suitable light guide including, for example, a liquid light guide or a fiberoptic bundle. The control board of the light source may be configured to control the optical power incident on the target tissue. In surgical use, a surgical drape may be placed over the light guide and filter/focusing apparatus to help ensure sterility. Alternatively or in addition, the light guide and the filter/focusing apparatus may be sterilizable and/or may be designed for one-time use. The emitters may emit light at wavelengths of, for example, 405nm, 495nm, 546nm, 635nm and white light. Any other suitable wavelengths or wavelength ranges and combinations thereof may be used.

FIG. 19b illustrates details of an emitter in the light source. In this example, the emitter may be a LED module. As shown, each emitter includes a bank of LEDs provided on a heat sink (which may be cooled with air flow, for example from cooling fans). Light from individual LEDs is collected at a converging lens and focused onto a respective branch of the multi-furcated light guide. Although a bank of three LEDs is shown in this example, more or less LEDs may be used, depending on the intensity of light desired. Although a converging lens is shown, other optics components may be used for focusing light from the emitter onto the light guide.

The example filter/focusing apparatus, the cross-section of which is shown in FIG. 19c, may direct light from the light guide through a filter (e.g., a shortpass filter, for example for wavelengths less than about 650nm) to reject any stray light in the fluorescence emission band, and through one or more optics components, such as an aspheric lens or other suitable lens, to shape the light emitted from the light source into a desired illumination shape and/or size. The light source may further include a translation mechanism such that the focusing optics component(s) may be translated relative to the beam from the light guide, such that the size of the beam emitted from the light source may be adjustable. There may be an attachment mechanism for attaching the apparatus to the surgical microscope. Any other suitable configuration for the filter/focusing apparatus may be used, in order to provide a way to adjust the diameter of the beam spot illuminating the target tissue. The shortpass filter may be any suitable filter that rejects any fluorescence generated in the light guide, as well as rejecting excitation leakage into the emission bands.

Figure 20:
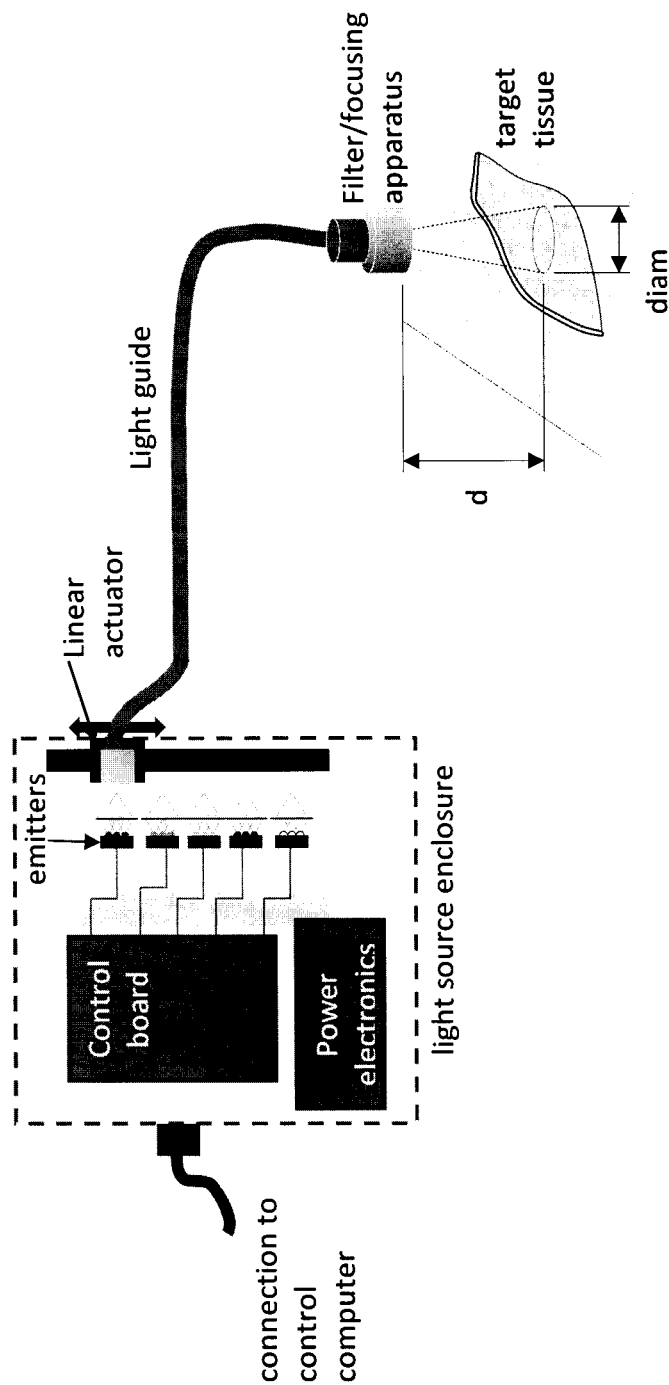
FIG. 20 is a schematic of another example light source suitable for use in an example imaging system.

FIG. 20 illustrates another example light source that may be suitable for providing the multi-spectral excitation light for one or more of the imaging systems described above. The example light source of FIG. 20 may be similar to that of FIGS. 19a-c, and the description with respect to FIGS. 19a-c may apply, with the difference that in the example of FIG. 20, a non-multi-furcated light guide (i.e., a one-to-one light guide) is mechanically shuttled back-and-forth between emitters (e.g., LED modules), for example using a linear actuator. This motorized switching may allow light from the light source to selectively emit light at different wavelengths or wavelength ranges.

FIGS. 21a-e illustrate an example of how depth-resolved detection may be accomplished using an example fiberoptic probe in contact with the target tissue. In this example, a multi-fiberoptic probe is used, which may be configured with the fibers arranged at the contact surface of the probe, for example as shown in the contact surface view of FIG. 21b. The example system has been simplified, and in this simplified illustration, there is a plurality of emitters for different excitation wavelengths (including white light) which are controlled (e.g., via control lines) by a processing computer to sequentially illuminate the target tissue via the fiberoptic probe. There is also a detector (or spectrometer) that detects light from the target tissue via the fiberoptic probe, which communicates data with the computer (e.g., via control lines).

Figure 21:
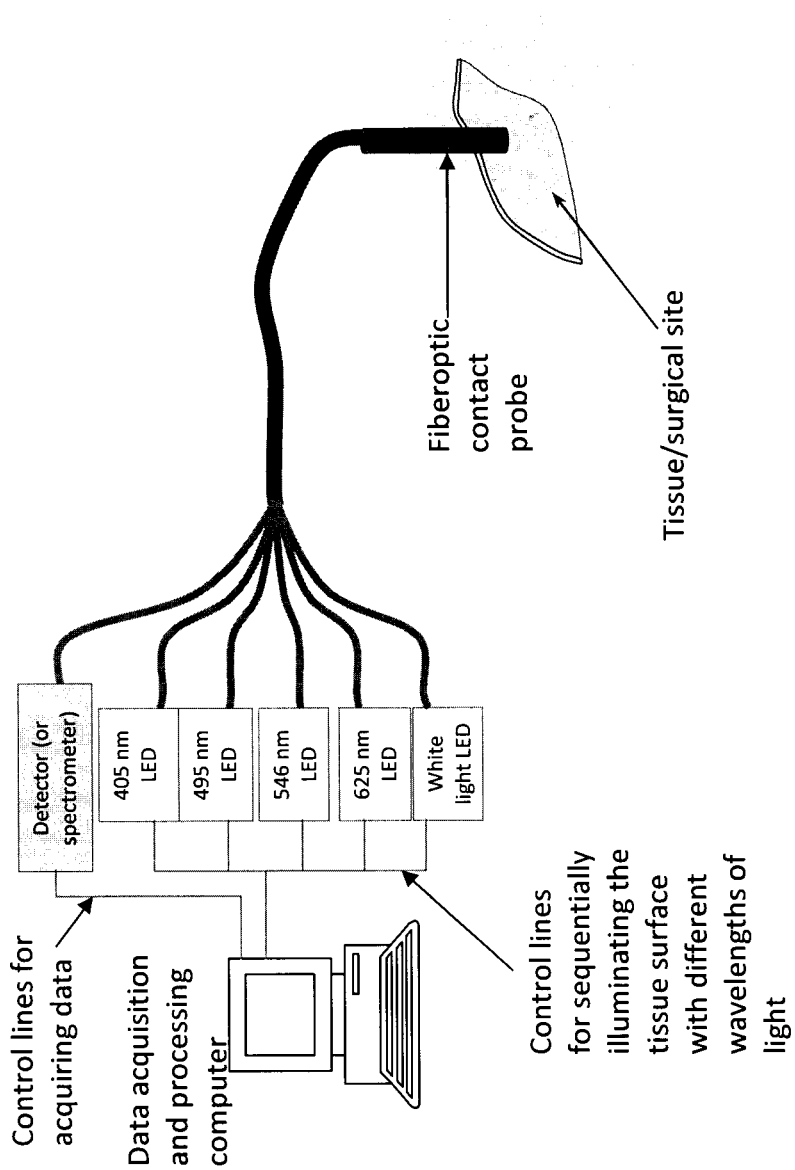
FIGS. 21a-e illustrate the use of an example fiberoptic probe in an example imaging system.
Figure 21:
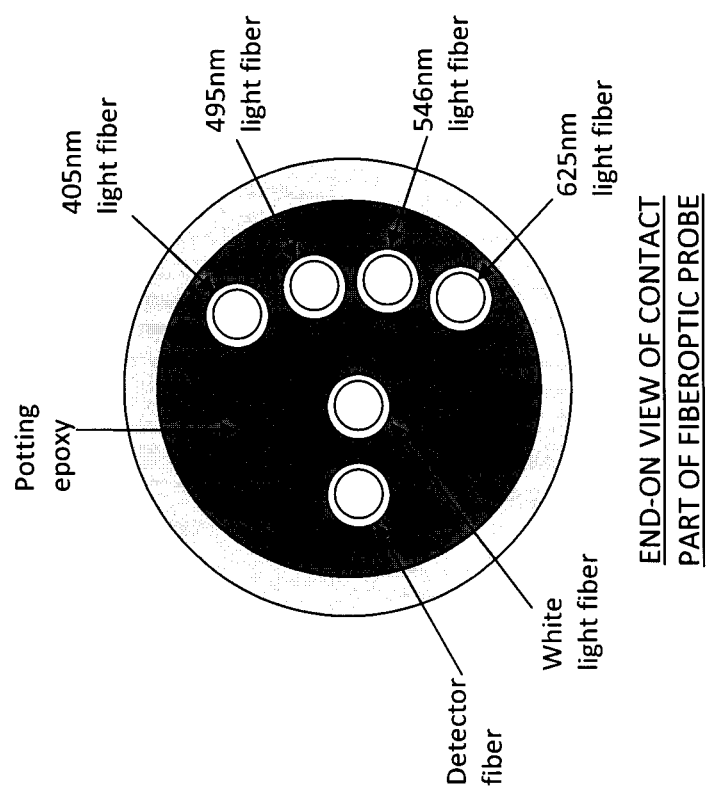
Figure 21:
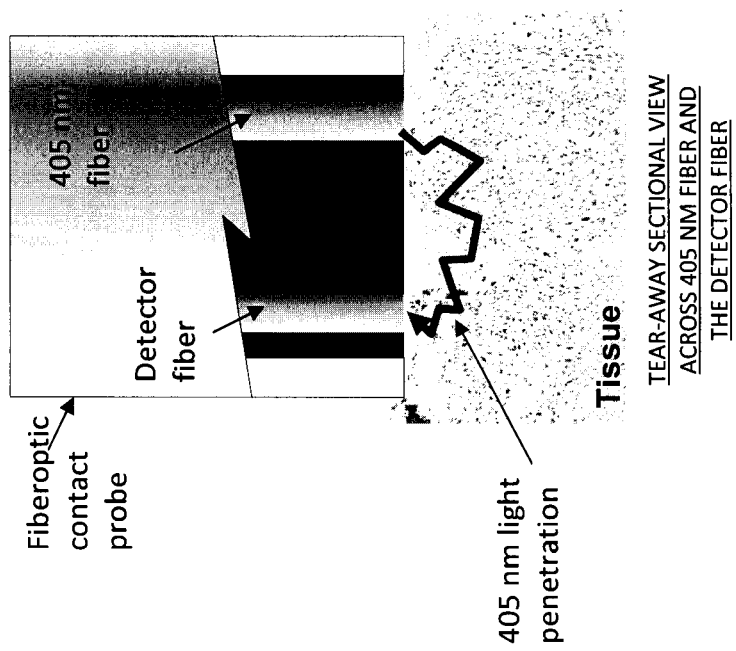
Figure 21:
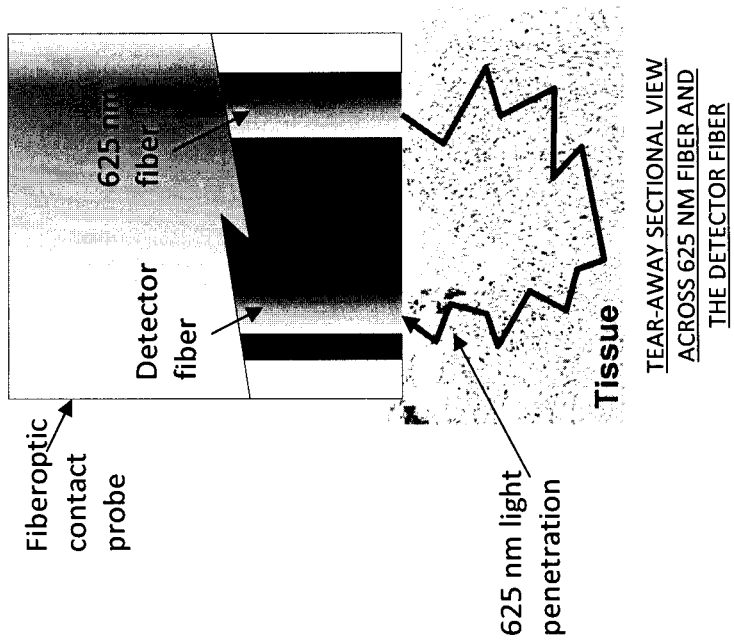
Figure 21:
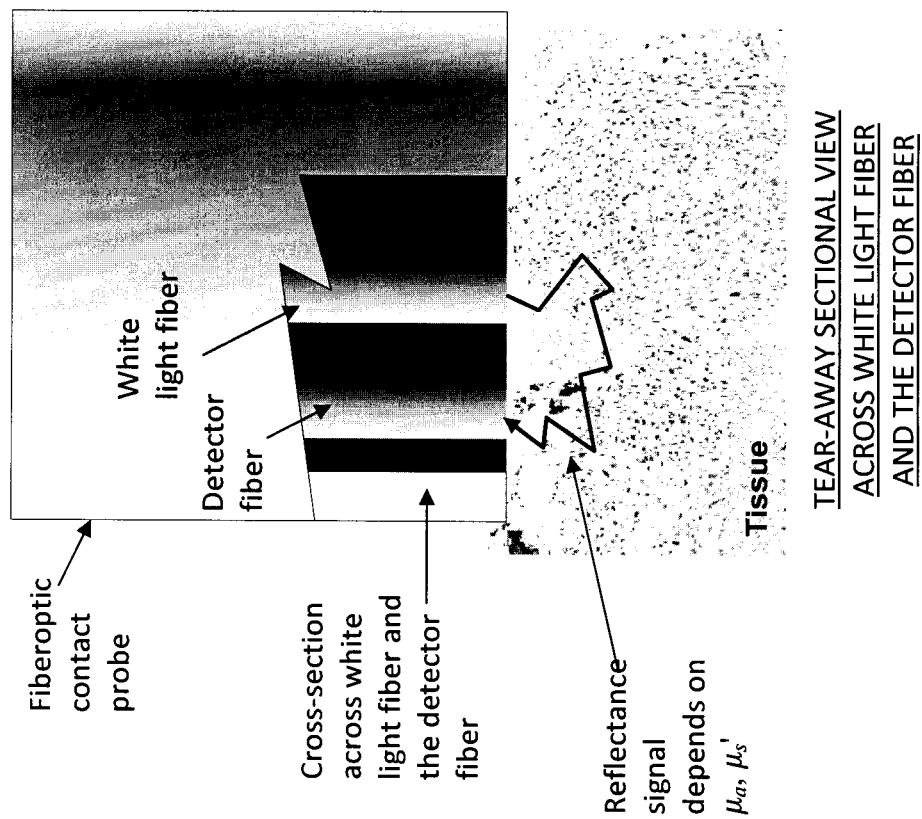

In this example, a detector fiber may be positioned at relatively equal distance or variable distances from, for example, four fibers each emitting light at different wavelengths or wavelength ranges. In FIG. 21b, there are four fibers, which emit light at 405nm, 495nm, 546nm and 625nm, respectively. In this example, the fiberoptic detection modality may be similar to the imaging modality configured described with reference to FIGS. 1-4, for example.

The example system having a fiberoptics probe may operate similarly to, for example, the example system of FIG. 1, except using a contact detection technique. The use of fiberoptics may allow for the measurement of tissue optical properties using well-established fiberoptic techniques. The use of fiberoptic techniques may be useful for various reasons, which may include, for example: 1) improved fluorescence signal detection due to closer contact with the tissue; 2) where the detection optical fiber is connected to a spectrometer, reduction or elimination of any autofluorescence background may more easily accomplished; 3) a fixed detection geometry relative to the tissue may allow for more robust calculations; and 4) a tissue optical properties measurement may be taken coincident to the multi-spectral excitation measurements. The use of the fiberoptic technique may be useful for applications where sensitivity to deeper (e.g., deeper than about 3.5mm, as used for imaging brain tissue) sub-surface fluorescence is desired. For example, if it is suspected that a brain tumor mass exists about 4-10 mm below the surgical surface, the fiberoptic contact technique, using the fiberoptic probe, may be useful. The use of a fiberoptic contact probe may limit detection to single-point detection, which may not be suitable for some applications. In some examples, the fiberoptic probe may be used interstitially, for example depending on the tissue of interest.

FIGS. 21c-d illustrate how light at different wavelengths (e.g., 405nm and 625nm) have different depths of penetration into a target tissue. As shown, shorter wavelength light (e.g., at 405nm) has shallower penetration into the tissue than longer wavelength light (e.g., at 625nm). The result of this difference in depth penetration is that depth information of sub-surface fluorescence from the tissue may be encoded in the different detected fluorescence resulting from each excitation wavelength.

In addition, a white light-emitting fiber may be positioned on the contact surface at a predetermined distance from the detector fiber. The white light-emitting fiber may be used to obtain an estimate of the tissue optical properties using suitable techniques, such as the technique of spectrally-constrained diffuse reflectance (e.g., as described by Kim et al., 2010). As shown in the example of FIG. 21e, the white light diffuse reflectance spectrum depends on the wavelength-dependent tissue optical properties (e.g., $\mu_a$, $\mu_s'$). Thus, the tissue optical properties may be estimated using diffuse reflectance measurements. Other suitable techniques may be used. These estimated optical properties may be used as inputs into a depth-estimation algorithm, similar to their input into equations 3, 6 and 7, that describe the imaging geometry.

In this example, the lead from the fiberoptic probe may split off into the individual fibers corresponding to the fibers positioned at the contact surface (e.g., as shown in FIG. 21b). The detector fiber may be connected to a light detector or a spectrometer. Each of the emitter fibers (e.g., the 405nm fiber, the 495nm fiber, the 546nm fiber, the 625nm fiber and the white light-emitting fiber) may be attached to switchable emitters (e.g., LEDs). A computer-controlled system may be used to switch each emitter on in sequence, such that the detector records the diffuse fluorescence at multiple excitation wavelengths or wavelength ranges.

While the present description provides certain examples, those of ordinary skill will understand and appreciate the existence of variations, combinations, and equivalents of the specific embodiment, method, and examples herein. Any embodiment, method, and examples described are for the purpose of illustration only and are not intended to be limiting. Any theory, equations or models described are for the purpose of illustration only and the present disclosure is not reliant on these. Features described in separate examples and embodiments may be used in combination. For any ranges disclosed, all values and sub-ranges are also hereby disclosed. All references mentioned are hereby incorporated by reference in their entirety.

References

J. Swartling, J. Svensson, D. Bengtsson, K. Terike, S. Andersson-Engels, "Fluorescence spectra provide information on the depth of fluorescent lesions in tissue," Appl. Opt., 44, 1934-41 (2005).

D. Hyde, T. J. Farrell, M. S. Patterson, B. C. Wilson. "A diffusion theory model of spatially resolved fluorescence from depth-dependent fluorophore concentrations," Phys. Med. Biol., 46, 369-83 (2001).

D. C. Comsa, T. J. Farrell, M. S. Patterson, "Quantitative fluorescence imaging of point-like sources in small animals," Phys. Med. Biol. 53, 5797-814 (2008).

E. M. Hillman, D. A. Boas, A. M. Dale, A. K. Dunn, "Laminar optical tomography: demonstration of millimeter-scale depth-resolved imaging in turbid media," Opt. Lett. 29, 1650-2. (2004).

D. S. Kepshire, S. C. Davis, H. Dehghani, K. D. Paulsen, B. W. Pogue, "Sub-surface diffuse optical tomography can localize absorber and fluorescent objects but recovered image sensitivity is nonlinear with depth," Appl. Opt. 46, 1669-78 (2007).

Arridge S R. "Optical tomography in medical imaging," Inv. Prob. 15, R41-R93 (1999).

T. J. Farrell, M. S. Patterson, "Diffusion modeling of fluorescence in tissue," in *Handbook of Biomedical Fluorescence*, eds. M. Mycek, B. W. Pogue, Marcel Dekker Inc. (2003).

T. J. Farrell, M. S. Patterson, B. C. Wilson, "A diffusion theory model of spatially resolved, steady-state diffuse reluctance for the non-invasive determination of tissue optical properties in vivo," Med. Phys. 19, 879-888 (1992).

F. A. J. Groenhuis, H. A. Ferwerda, J. J. ten Bosch, "Scattering and absorption of turbid materials derived from reflection coefficients. 1: Theory," Appl. Opt. 22, 2456-2462 (1983).

A. Kim, B. C. Wilson, "Measurement of ex vivo and in vivo tissue optical properties: Methods and theories," Chap. 8 in Optical-Thermal Response of Laser-Irradiated Tissue, A. J. Welch and M. J. C. van Gernert Eds., Dordrecht: Springer SBM (2010).

The invention claimed is:

1. A system for sub-surface fluorescence topographical imaging comprising:
    an excitation source for selectably emitting light at at least two excitation wavelengths or wavelength ranges at a target surface, the at least two excitation wavelengths or wavelength ranges comprising:
        a first excitation wavelength or wavelength range selected to provide a first depth of optical penetration, for causing fluorescing of a marker below the target surface; and
        a second excitation wavelength or wavelength range selected to provide a second depth of optical penetration different from the first depth of optical penetration, for causing fluorescing of the marker below the target surface; and
    a light detector for detecting fluorescence emission wavelengths or wavelength ranges from the target surface.

2. The system of claim 1 wherein the marker corresponds to an object having an object top surface layer at a sub-surface depth that faces towards the target surface, and fluorescing of the marker corresponding to the object top surface layer is detected by the light detector.

3. The system of claim 1 wherein the excitation source comprises a broadband light source and a plurality of excitation filters, each excitation filter being selectably positionable to filter light from the broadband light source in order to produce a respective one of the at least two excitation wavelengths or wavelength ranges.

4. The system of claim 1 wherein the excitation source comprises a plurality of light sources, each of the plurality of light sources being selectable for emitting a respective one of the at least two excitation wavelengths or wavelength ranges.

5. The system of claim 1 wherein the light detector comprises a detection filter positionable to filter emitted light from the target surface in order to restrict emission wavelengths detected by the light detector.

6. The system of claim 1 wherein the excitation source is configured to emit the at least two excitation wavelengths or wavelength ranges concurrently with frequency modulation.

7. The system of claim 1 wherein a turbid light-absorbing medium is below the target surface.

8. The system of claim 1 further comprising a fiberoptic probe housing fiberoptics for emitting the excitation wavelengths or wavelength ranges to the target surface and for receiving the fluorescence emission wavelengths or wavelength ranges.

9. The system of claim 1 further comprising a processor configured to execute instructions for:
    determining a fluorescence measurement for each of the at least two excitation wavelengths or wavelength ranges using the detected fluorescence emission wavelengths or wavelength ranges, and associating the fluorescence measurement with the respective depth of each of the at least two excitation wavelengths or wavelength ranges; and
    constructing a sub-surface fluorescence topographical image using the determined fluorescence measurements and associated depths.

10. The system of claim 5 wherein the detected fluorescence emission wavelengths or wavelength ranges correspond to a top surface layer of an object at a sub-surface depth, and constructing the sub-surface fluorescence topographical image comprises constructing a fluorescence topographical image of the top surface layer of the object.

11. The system of claim 1 further comprising a measurement probe for measuring at least one optical property of the target surface.

12. A method for sub-surface fluorescence imaging comprising:
    illuminating a target surface with light at at least two excitation wavelengths or wavelength ranges; the at least two excitation wavelengths or wavelength ranges comprising:
        a first excitation wavelength or wavelength range selected to provide a first depth of optical penetration, for causing fluorescing of a marker below the target surface; and
        a second excitation wavelength or wavelength range selected to provide a second depth of optical penetration different from the first depth of optical penetration, for causing fluorescing of the marker below the target surface; and;
    detecting fluorescence emission wavelengths or wavelength ranges from the target surface;
    determining a fluorescence calculation for each of the at least two excitation wavelengths or wavelength ranges using the detected fluorescence emission wavelengths or wavelength ranges; and
    constructing a sub-surface fluorescence topographical image using the determined fluorescence calculations.

13. The method of claim 12 wherein the detected fluorescence emission wavelengths or wavelength ranges correspond to a top surface layer of an object at a sub-surface depth, and constructing the sub-surface fluorescence topographical image comprises constructing a fluorescence topographical image of the top surface layer of the object.

14. The method of 12 wherein the target surface is successively illuminated with the at least two excitation wavelengths or wavelength ranges.

15. The method of claim 12 wherein the target surface is simultaneously illuminated with the at least two excitation wavelengths or wavelength ranges, the at least two excitation wavelengths or wavelength ranges being frequency modulated.

16. The method of claim 12 further comprising:
    illuminating the target surface with light over a major portion of the emission wavelengths or wavelength ranges;
    measuring a background reflectance from the target surface;
    wherein constructing the sub-surface fluorescence topographical image accounts for the background reflectance.

17. The method of claim 16 wherein the light over the major portion of the emission wavelengths or wavelength ranges is broadband white light.

18. The method of claim 12 wherein the fluorescence calculation is one of:
- a ratio of detected fluorescence for each excitation wavelength or wavelength ranges to a reference measured emitted fluorescence for a reference excitation wavelength or wavelength ranges; and
- a depth range for each detected fluorescence associated with the respective depth of each excitation wavelength or wavelength range.

19. The method of claim 18 wherein the fluorescence calculation is used in a sub-surface fluorescence model to construct the sub-surface fluorescence topographical image.

20. The method of claim 12 further comprising:
detecting at least one optical property of the target surface relevant to the sub-surface fluorescence model.

21. The method of claim 12 further comprising: providing a fluorescence marker as the marker.

22. The method of claim 12 wherein a turbid light-absorbing medium is below the target surface.

* * * * *